(12) United States Patent
Gourguechon et al.

(10) Patent No.: US 10,538,758 B2
(45) Date of Patent: Jan. 21, 2020

(54) CAPTURE OF NUCLEIC ACIDS USING A NUCLEIC ACID-GUIDED NUCLEASE-BASED SYSTEM

(71) Applicant: Arc Bio, LLC, Cambridge, MA (US)

(72) Inventors: Stephane B. Gourguechon, Cambridge, MA (US); Eric Harness, Cambridge, MA (US); David Sinclair, Cambridge, MA (US); Meredith L. Carpenter, Cambridge, MA (US)

(73) Assignee: Arc Bio, LLC, Cambridge, MA (US)

( * ) Notice: Subject to any disclaimer, the term of this patent is extended or adjusted under 35 U.S.C. 154(b) by 0 days.

(21) Appl. No.: 15/520,052

(22) PCT Filed: Aug. 18, 2016

(86) PCT No.: PCT/US2016/047631
§ 371 (c)(1),
(2) Date: Apr. 18, 2017

(87) PCT Pub. No.: WO2017/031360
PCT Pub. Date: Feb. 23, 2017

(65) Prior Publication Data
US 2018/0312830 A1    Nov. 1, 2018

Related U.S. Application Data

(60) Provisional application No. 62/207,359, filed on Aug. 19, 2015.

(51) Int. Cl.
| | | |
|---|---|---|
| *C12N 15/10* | (2006.01) | |
| *C12N 9/12* | (2006.01) | |
| *C12N 9/22* | (2006.01) | |
| *C12Q 1/686* | (2018.01) | |

(52) U.S. Cl.
CPC .......... *C12N 15/10* (2013.01); *C12N 9/1276* (2013.01); *C12N 9/22* (2013.01); *C12N 2310/20* (2017.05); *C12Q 1/686* (2013.01); *C12Q 2521/301* (2013.01); *C12Q 2525/191* (2013.01)

(58) Field of Classification Search
None
See application file for complete search history.

(56) References Cited

U.S. PATENT DOCUMENTS

| | | | |
|---|---|---|---|
| 5,948,902 | A | 9/1999 | Honkanen et al. |
| 9,249,460 | B2 | 2/2016 | Pushkarev et al. |
| 9,725,765 | B2 | 8/2017 | Pushkarev et al. |
| 2005/0053947 | A1 | 3/2005 | Hager et al. |
| 2005/0233340 | A1 | 10/2005 | Barrett et al. |
| 2009/0318305 | A1 | 12/2009 | Lin et al. |
| 2013/0298265 | A1 | 11/2013 | Cunnac et al. |
| 2014/0045705 | A1 | 2/2014 | Bustamante et al. |
| 2014/0068797 | A1 | 3/2014 | Doudna et al. |
| 2014/0134610 | A1 | 5/2014 | Pham et al. |
| 2014/0186843 | A1 | 7/2014 | Zhang et al. |
| 2014/0356867 | A1 | 12/2014 | Peter et al. |
| 2014/0357523 | A1 | 12/2014 | Zeiner et al. |
| 2015/0031089 | A1 | 1/2015 | Lindstrom |
| 2015/0071901 | A1 | 3/2015 | Liu et al. |
| 2015/0133391 | A1 | 5/2015 | de Vlaminick et al. |
| 2015/0211058 | A1 | 7/2015 | Carstens |
| 2015/0225773 | A1 | 8/2015 | Farmer et al. |
| 2015/0232834 | A1 | 8/2015 | Bustamante et al. |
| 2015/0360194 | A1 | 12/2015 | Bustamante et al. |
| 2016/0017396 | A1 | 1/2016 | Cann et al. |
| 2016/0053304 | A1 | 2/2016 | Wurtzel et al. |
| 2016/0208241 | A1 | 7/2016 | Tsai et al. |
| 2017/0016048 | A1 | 1/2017 | Blauwkamp et al. |
| 2017/0088887 | A1 | 3/2017 | Makarov et al. |
| 2018/0051320 | A1 | 2/2018 | DeRisi et al. |
| 2018/0237851 | A1 | 8/2018 | Christians et al. |
| 2018/0298421 | A1 | 10/2018 | Carpenter et al. |
| 2019/0144920 | A1 | 5/2019 | Carpenter et al. |

FOREIGN PATENT DOCUMENTS

| | | |
|---|---|---|
| EP | 2 635 679 B1 | 4/2017 |
| WO | WO-2013/141680 A1 | 9/2013 |
| WO | WO-2013/142578 A1 | 9/2013 |
| WO | WO-2013/191775 A2 | 12/2013 |
| WO | WO-2013/191775 A3 | 12/2013 |
| WO | WO-2014/189957 A2 | 11/2014 |
| WO | WO-2014/189957 A3 | 11/2014 |
| WO | WO-2015/070083 A1 | 5/2015 |
| WO | WO-2015/075056 A1 | 5/2015 |
| WO | WO-2015/119941 A2 | 8/2015 |
| WO | WO-2015/119941 A3 | 8/2015 |
| WO | WO-2015/122967 A1 | 8/2015 |
| WO | WO-2016/014409 A1 | 1/2016 |
| WO | WO-2016/028843 A2 | 2/2016 |
| WO | WO-2016/028843 A3 | 2/2016 |
| WO | WO-2016/100955 A2 | 6/2016 |

(Continued)

OTHER PUBLICATIONS

Yamano et al. Cell 2016; 165: 949-962 (Year: 2016).*
Mougiakos et al. Trends in Biotechnology 2016; 34: 575-587 (Year: 2016).*
Cebrian-Serrano, A. and Davies, B. Mammalian Genome 2017; 28: 247-261 (Year: 2017).*
Gasiunas et al. Proceedings of the National Academy of Sciences, USA 2012; 109: E2579-2586 (Year: 2102).*
Fonfara et al. Nucleic Acids Research 2014; 42: 2577-2590 (Year: 2014).*
Javidi-Parsijani et al. PLoS ONE 2017; 12: e0177444 (Year: 2017).*
Swarts et al. Molecular Cell 2017; 66: 221-233 (Year: 2017).*
Zetsche et al. Cell 2015; 163: 759-771 (Year: 2015).*
Briner, A.E. et al. (2014). "Guide RNA functional modules direct Cas9 activity and orthogonality," *Mol. Cell.* 56(2):333-339.

(Continued)

*Primary Examiner* — Angela M. Bertagna
(74) *Attorney, Agent, or Firm* — Cooley LLP; Mike Reiner Mayer; Madhuri Roy

(57) ABSTRACT

Provided herein are methods and compositions for the capture of nucleic acids, for example by using a nucleic acid-guided nuclease-based system.

10 Claims, 13 Drawing Sheets

Specification includes a Sequence Listing.

(56) References Cited

FOREIGN PATENT DOCUMENTS

| WO | WO-2016/100955 A3 | 6/2016 |
| WO | WO-2016/196805 A1 | 12/2016 |
| WO | WO-2017/031360 A1 | 2/2017 |
| WO | WO-2017/062599 A1 | 4/2017 |
| WO | WO-2017/066588 A2 | 4/2017 |
| WO | WO-2017/066588 A3 | 4/2017 |
| WO | WO-2018/035062 A1 | 2/2018 |
| WO | WO-2018/069430 A1 | 4/2018 |

OTHER PUBLICATIONS

Day, K. et al. (2014). "Targeted sequencing of large genomic regions with CATCH-Seq," *PLoS One* 9(10):e111756.

Feehery, G.R. et al. (2013). "A method for selectively enriching microbial DNA from contaminating vertebrate host DNA," *PLoS One* 8(10):e76096.

Gu, W. et al. (2016). "Depletion of Abundant Sequences by Hybridization (DASH): Using Cas9 to remove unwanted high-abundance species in sequencing libraries and molecular counting applications," *Genome Biology* 17:41.

International Search Report dated May 3, 2016, for PCT Application No. PCT/US2015/066949, filed on Dec. 19, 2015, 4 pages.

International Search Report dated Dec. 20, 2016, for PCT Application No. PCT/US2016/047631, filed on Aug. 18, 2016, 5 pagese.

Malina, A. et al. (2013). "Repurposing CRISPR/Cas9 for in situ functional assays," *Genes Dev.* 27(23):2602-2614.

Ran, F.A. et al. (2015). "In vivo genome editing using *Staphylococcus aureus* Cas9," *Nature* 520(7546):186-191.

Smolina, I.V. et al. (2005). "End invasion of peptide nucleic acids (PNAs) with mixed-base composition into linear DNA duplexes," *Nuc. Acids Res.* 33(17):e146.

Swarts, D.C. et al. (2014). "DNA-guided DNA interference by a prokaryotic Argonaute," *Nature* 507(7491):258-261.

Written Opinion of the International Searching Authority dated May 3, 2016, for PCT Application No. PCT/US2015/066949, filed on Dec. 19, 2015, 10 pages.

Written Opinion of the International Searching Authority dated Dec. 20, 2016, for PCT Application No. PCT/US2016/047631, filed on Aug. 18, 2016, 12 pages.

Wu, J. et al. (2014). "OsLOL1, a C2C2-type zinc finger protein, interacts with OsbZIP58 to promote seed germination through the modulation of gibberellin biosynthesis in *Oryza sativa*," *Plant J.* 80(6):1118-1130.

Ma, M. et al. (2013). "A guide RNA sequence design platform for the CRISPR/Cas9 system for model organism genomes," *Biomed. Res. Int.* 2013, p. 1-4, 4 total pages.

Gasiunas, G. et al. (2012). "Cas9-crRNA ribonucleoprotein complex mediates specific DNA cleavage for adaptive immunity in bacteria," *PNAS* 109:E2579-2586.

Jinek, M. et al. (2012). "A programmable dual-RNA-guided DNA endonuclease in adaptive bacterial immunity," *Science* 337:816-821.

Shmakov, S. et al. (2015). "Discovery and Functional Characterization of Diverse Class 2 CRISPR-Cas Systems," *Mol. Cell.* 60:385-397.

Fu, Y. et al. (2014). "Improving CRISPR-Cas nuclease specificity using truncated guide RNAs," *Nat. Biotechnol.* 32:279-284.

Ran, F.A. et al. (2013). "Genome engineering using the CRISPR-Cas9 system," *Nat. Protoc.* 8:2281-2308.

Garneau, J.E. et al. (2010). "The CRISPR/Cas bacterial immune system cleaves bacteriophage and plasmid DNA," *Nature* 468:67-71.

O'Connell, M.R. et al. (2014). "Programmable RNA recognition and cleavage by CRISPR/Cas9," *Nature* 516:263-266.

Kleinstiver, B.P. et al. (2015). "Engineered CRISPR-Cas9 nucleases with altered PAM specificities," *Nature* 523:481-485.

Sternberg, S.H. et al. (2015). "Conformational control of DNA target cleavage by CRISPR-Cas9," *Nature* 527:110-113.

Cencic, R. et al. (2014). "Protospacer adjacent motif (PAM)-distal sequences engage CRISPR Cas9 DNA target cleavage," *PLoS One* 9:e109213, 13 total pages.

Shalem, O. et al. (2014). "Genome-scale CRISPR-Cas9 knockout screening in human cells," *Science* 343:84-87.

Wang, T. et al. (2013). "Genetic screens in human cells using the CRISPR-Cas9 system," *Science* 343:80-84.

Fusi, N. et al. (2015). "In silico predictive modeling of CRISPR/Cas9 guide efficiency," *bioRxiv* p. 1-31.

Jinek, M. et al. (2013). "RNA-programmed genome editing in human cells," *Elife* e00471, pp. 1-9.

Cong, L. et al. (2013). "Multiplex genome engineering using CRISPR/Cas systems," *Science* 339:819-823.

Buenrostro, J.D. et al. (2013). "Transposition of native chromatin for multimodal regulatory analysis and personal epigenomics," *Nature Methods* 10:1213-1218. epub doi:10.1038/nmeth.2688, pp. 1-15 provided.

Carpenter, M.L. et al, (2013). "Pulling out the 1%: whole-genome capture for the targeted enrichment of ancient DNA sequencing libraries," *Am. J. Human Genet.* 93:852-864.

Dolinsek, J. et al. (2013). "Depiction of unwanted nucleic acid templates by selective cleavage: LNAzyrnes, catalytically active oligonucleotides containing locked nucleic acids, open a new window for detecting rare microbial community members," *App. Environ. Microbiol.* 79:1534-1544.

Extended European Search Report dated Apr. 20, 2018, for EP Application No. 15 871 259.6, filed on Dec. 19, 2015, 12 pages.

Extended European Search Report dated Jan. 8, 2019, for EP Application No. 16 837 863.6, flied on Aug. 18, 2016, 6 pages.

Fujita, T. and Fujii H. (2013). "Efficient isolation of specific genomic regions and identification of associated proteins by engineered DNA-binding molecule-mediated chromatin immunoprecipitation (enChIP) using CRISPR," *Biochem. Biophys. Res. Commun.* 439:132-136.

Loman, N.J. et al. (2012). "High-throughput bacterial genome sequencing: an embarrassment of choice, a world of opportunity," *Nature Review Microbiol.* 10:599-606.

Moylan, J.D. et al. (2012). "Selective depletion of rRNA enables whole transcriptome profiling of archival fixed tissue," *PioS One* 7:e42882. pp. 1-8 provided.

Non-Final Office Action dated Jul. 5, 2019, for U.S. Appl. No. 15/537,962, filed Jun. 20 2017, 16 pages.

Non-Final Office Action dated Jul. 5, 2019, for U.S. Appl. No. 16/231,338, filed Dec. 21, 2018, 15 pages.

\* cited by examiner

CAPTURE OF NUCLEIC ACIDS USING A NUCLEIC ACID-GUIDED NUCLEASE-BASED SYSTEM

CROSS REFERENCE TO RELATED APPLICATIONS

This is a U.S. National Stage Application under 35 U.S.C. § 371 of International Application No. PCT/US2016/047631, filed on Aug. 18, 2016, which claims priority to U.S. Provisional Application Ser. No. 62/207,359, filed on Aug. 19, 2015, each of which is incorporated herein by reference in its entirety.

INCORPORATION OF THE SEQUENCE LISTING

The contents of the text file named "ARCB_00201US_SeqList.txt", which was created on Dec. 31, 2018 and is 6 KB in size, are hereby incorporated by reference in their entirety.

BACKGROUND OF THE INVENTION

Targeted sequencing of specific regions of the genome continues to be of interest to researchers, particularly in a clinical setting. Clinical diagnosis of genetic disease, cancer, and many research projects rely on targeted sequencing to enable high coverage sequencing of targeted sites while reducing sequencing costs. Currently, the primary methods used for this purpose are 1) hybridization-based enrichment, and 2) multiplex PCR. In the former approach, biotin-labeled short oligonucleotide probes are used to "pull out" sequences of interest from a library. This process can be time-consuming, expensive, and require many hands-on steps. Furthermore, often some "off-target" sequences can remain in the resulting product. The multiplex PCR-based approach can be faster, but the number of targets can be limited and the cost can be high. Needed are methods for the efficient capture of nucleic acid regions of interest that are easy, specific, rapid, and inexpensive. Provided herein are methods and compositions that address this need.

All patents, patent applications, publications, documents, web links, and articles cited herein are incorporated herein by reference in their entireties.

BRIEF SUMMARY OF THE INVENTION

Provided herein are methods and compositions that allow for the selective capture of nucleic acid sequences of interest. The nucleic acids may contain DNA or RNA. The methods and compositions provided herein are particularly useful for working with complex nucleic acid samples.

In one aspect, the invention provides a method of capturing target nucleic acid sequences comprising: (a) providing a sample comprising a plurality of adapter-ligated nucleic acids, wherein the nucleic acids are ligated to a first adapter at one end and ligated to a second adapter at the other end; (b) contacting the sample with a plurality of nucleic acid-guided nuclease-gNA complexes, wherein the gNAs are complementary to targeted sites of interest contained in a subset of the nucleic acids, thereby generating a plurality of nucleic acid fragments ligated to a first or second adapter at one end and no adapter at the other end; (c) contacting the plurality of nucleic acid fragments with third adapters, thereby generating a plurality of nucleic acid fragments ligated to either the first or second adapter at one end and the third adapter at the other end. In one embodiment, the nucleic acid-guided nuclease is a CRISPR/Cas system protein. In one embodiment, the nucleic acid-guided nuclease is a non-CRISPR/Cas system protein. In one embodiment, the nucleic acid-guided nuclease is selected from the group consisting of CAS Class I Type I, CAS Class I Type III, CAS Class I Type IV, CAS Class II Type II, and CAS Class II Type V. In one embodiment, the nucleic acid-guided nuclease is selected from the group consisting of Cas9, Cpf1, Cas3, Cas8a-c, Cas10, Cse1, Csy1, Csn2, Cas4, Csm2, Cm5, Csf1, C2c2, and NgAgo. In one embodiment, the gNAs are gRNAs. In one embodiment, the gNAs are gDNAs. In one embodiment, the contacting with a plurality of nucleic acid-guided nuclease-gNA complexes cleaves the targeted sites of interest contained in a subset of the nucleic acids, thereby generating a plurality of nucleic acid fragments comprising a first or second adapter at one end and no adapter at the other end. In one embodiment the method further comprises amplifying the product of step (c) using first or second and third adapter-specific PCR. In one embodiment the nucleic acids are selected from the group consisting of single stranded DNA, double stranded DNA, single stranded RNA, double stranded RNA, and a DNA/RNA hybrid. In one embodiment the nucleic acids are double stranded DNA. In one embodiment the nucleic acids are from genomic DNA. In one embodiment the genomic DNA is human. In one embodiment the nucleic acids adapter-ligated ends are from 20 bp to 5000 bp in length. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment amplified products are used for cloning, sequencing, or genotyping. In one embodiment the adapters are from 20 bp to 100 bp in length. In one embodiment the adapters comprise primer binding sites. In one embodiment the adapters comprise sequencing adapters or restriction sites. In one embodiment the targeted sites of interest represent less than 50% of the total nucleic acid in the sample. In one embodiment the sample is obtained from a biological sample a clinical sample, a forensic sample, or an environmental sample. In one embodiment the first and second adapters are identical. In one embodiment the first and second adapters are different. In one embodiment the sample comprises a sequencing library.

In another aspect, the invention provides a method of introducing labeled nucleotides at targeted sites of interest comprising: (a) providing a sample comprising a plurality of nucleic acid fragments; (b) contacting the sample with a plurality of nucleic acid-guided nuclease nickase-gNA complexes wherein the gNAs are complementary to targeted sites of interest in the nucleic acid fragments, thereby generating a plurality of nicked nucleic acid fragments at the targeted sites of interest; and (c) contacting the plurality of nicked nucleic acid fragments with an enzyme capable of initiating nucleic acid synthesis at a nicked site, and labeled nucleotides, thereby generating a plurality of nucleic acid fragments comprising labeled nucleotides in the targeted sites of interest. In one embodiment, the nucleic acid-guided nuclease nickase is selected from the group consisting of CAS Class I Type I nickase, CAS Class I Type III nickase, CAS Class I Type IV nickase, CAS Class II Type II nickase, and CAS Class II Type V nickase. In one embodiment, the nucleic acid-guided nuclease nickase is selected from the group consisting of Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, and NgAgo nickase. In one embodiment, the gNAs are gRNAs. In one embodiment, the gNAs are gDNAs. In one embodiment the nucleic acid fragments are selected from the group consisting of single stranded DNA fragments, double stranded DNA fragments, single stranded RNA fragments, double stranded RNA fragments, and a DNA/RNA hybrid fragments. In one embodiment the nucleic fragments are double stranded DNA fragments. In one embodiment double stranded DNA fragments are from genomic DNA. In one embodiment the genomic DNA is human. In one embodiment the nucleic acid fragments are from 20 bp to 5000 bp in length. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment the targeted sites of interest represent less than 50% of the total nucleic acid in the sample. In one embodiment the sample is obtained from a biological sample, a clinical sample, a forensic sample, or an environmental sample. In one embodiment the labeled nucleotides are biotinylated nucleotides. In one embodiment, the labeled nucleotides are part of an antibody conjugate pair. In one embodiment the method further comprises contacting the nucleic acid fragments comprising biotinylated nucleotides with avidin or strepavidin, thereby capturing the targeted nucleic acid sites of interest. In one embodiment the enzyme capable of initiating nucleic acid synthesis at a nicked site is DNA Polymerase I, a Klenow fragment, a TAQ polymerase, or a Bst DNA Polymerase. In one embodiment the Cas9 nickase nicks the 5' end of the nucleic acid fragments. In one embodiment the nucleic acid fragments are from 20 bp to 5000 bp in length. In one embodiment the sample is obtained from a biological sample a clinical sample, a forensic sample, or an environmental sample.

In another aspect, the invention provides a method of capturing target nucleic acid sequences of interest comprising: (a) providing a sample comprising a plurality of adapter-ligated nucleic acids, wherein the nucleic acids are ligated to a first adapter at one end and are ligated to a second adapter at the other end; and (b) contacting the sample with a plurality of catalytically dead nucleic acid-guided nuclease-gNA complexes, wherein the catalytically dead nucleic acid-guided nuclease is fused to a transposase, wherein the gRNAs are complementary to targeted sites of interest contained in a subset of the nucleic acids, and wherein the complexes are loaded with a plurality of third adapters, to generate a plurality of nucleic acids fragments comprising either a first or second adapter at one end, and a third adapter at the other end. In one embodiment the method further comprises amplifying the product of step (b) using first or second adapter and third adapter-specific PCR. In one embodiment, the catalytically dead nucleic acid-guided nuclease is derived from a CRISPR/Cas system protein. In one embodiment, the catalytically dead nucleic acid-guided nuclease is derived from a non-CRISPR/Cas system protein. In one embodiment, the catalytically-dead nucleic acid-guided nuclease is selected from the group consisting of dead CAS Class I Type I, dead CAS Class I Type III, dead CAS Class I Type IV, dead CAS Class II Type II, and dead CAS Class II Type V. In one embodiment, the catalytically dead nucleic acid-guided nuclease is selected from the group consisting of dCas9, dCpf1, dCas3, dCas8a-c, dCas10, dCse1, dCsy1, dCsn2, dCas4, dCsm2, dCm5, dCsf1, dC2C2, and dNgAgo. In one embodiment, the gNAs are gRNAs. In one embodiment, the gNAs are gDNAs. In one embodiment the nucleic acids sequences are from genomic DNA. In one embodiment the genomic DNA is human. In one embodiment the catalytically dead nucleic acid-guided nuclease is fused to the N-terminus of the transposase. In one embodiment the catalytically dead nucleic acid-guided nuclease is fused to the C-terminus of the transposase. In one embodiment the adapter-ligated nucleic acids are 20 bp-5000 bp. In one embodiment the contacting of step (b) allows for the insertion of the second adapter into the targeted nucleic acid sequences. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment the amplified products are used for cloning, sequencing, or genotyping. In one embodiment the adapters are from 20 bp to 100 bp in length. In one embodiment the adapters comprise primer binding sites. In one embodiment the adapters comprise sequencing adapters or restriction sites. In one embodiment the targeted sites of interest represent less than 50% of the total nucleic acid in the sample. In one embodiment the sample is obtained from a biological sample a clinical sample, a forensic sample, or an environmental sample.

In another aspect, the invention provides a method of capturing target nucleic acid sequences of interest comprising: (a) providing a sample comprising a plurality of adapter-ligated nucleic acids, wherein the nucleic acids are ligated to the adapter at the 5' end and 3' ends; (b) contacting the sample with a plurality of catalytically dead nucleic acid-guided nuclease-gNA complexes, wherein the gNAs are complementary to targeted sites of interest contained in a subset of the nucleic acids, thereby generating a plurality of nucleic acids adapter-ligated at the 5' and 3' ends, bound to a catalytically dead nucleic acid-guided nuclease-gNA complex; and (c) contacting the sample with a plurality of catalytically dead nucleic acid-guided nuclease-gNA complexes, wherein the gNAs are complementary to both targeted sites of interest and targeted sites not of interest in the nucleic acids, thereby generating a plurality of nucleic acid fragments comprising nucleic acid sequences not of interest, adapter ligated at only one of the 5' or 3' ends. In one embodiment the contacting of step (c) does not displace the plurality of nucleic acids adapter-ligated at the 5' and 3' ends, bound to a dCAS9-gRNA complex of step (b). In one embodiment the contacting in step (d) cleaves the targeted sites not of interest contained in a subset of the nucleic acids, thereby generating a plurality of nucleic acid fragments comprising nucleic acid sequences not of interest, adapter ligated at only one of the 5' or 3' ends. In one embodiment the method further comprises removing the bound dCAS9-gRNA complex and amplifying the product of step (b) using adapter-specific PCR. In one embodiment the catalytically dead nucleic acid-guided nuclease is a CRISPR/Cas system protein. In one embodiment the catalytically dead nucleic acid-guided nuclease is a non-CRISPR/Cas system protein. In one embodiment, the catalytically-dead nucleic acid-guided nuclease is selected from the group consisting of dead CAS Class I Type I, dead CAS Class I Type III, dead CAS Class I Type IV, dead CAS Class II Type II, and dead CAS Class II Type V. In one embodiment the catalytically dead nucleic acid-guided nuclease is selected from the group consisting of dCas9, dCpf1, dCas3, dCas8a-c, dCas10, dCse1, dCsy1, dCsn2, dCas4, dCsm2, dCm5, dCsf1, dC2C2, and dNgAgo. In one embodiment the gNAs are gRNAs. In one embodiment the gNAs are gDNAs. In one embodiment the nucleic acids are selected from the group consisting of single stranded DNA, double stranded DNA, single stranded RNA, double stranded RNA, and a DNA/RNA hybrid. In one embodiment the nucleic acids are double stranded DNA. In one embodiment the nucleic acids are from genomic DNA. In one embodiment the genomic DNA is human. In one embodiment the nucleic acids adapter-ligated at the 5'ends and the 3'ends are from 20 bp to 5000 bp in length. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment the amplified products are used for cloning, sequencing, or genotyping. In one embodiment the adapters are from 20 bp to 100 bp in length. In one embodiment the adapters comprise primer binding sites. In one embodiment the adapters comprise sequencing adapters or restriction sites. In one embodiment the targeted sites of interest represent less than 50% of the total nucleic acid in the sample. In one embodiment the sample is obtained from a biological sample, a clinical sample, a forensic sample, or an environmental sample.

In another aspect, the invention provides a method of capturing target DNA sequences of interest comprising: (a) providing a sample comprising a plurality of nucleic acid sequences, wherein the nucleic acid sequences comprise methylated nucleotides, and wherein the nucleic acid sequences are adapter ligated on the 5' and 3' ends; (b) contacting the sample with a plurality of nucleic acid-guided nuclease nickase-gNA complexes, wherein the gNAs are complementary to targeted sites of interest in a subset of the nucleic acid sequences, thereby generating a plurality of nicked sites of interest in the subset of the nucleic acid sequences, and wherein the target nucleic acid sequences are adapter ligated on the 5' and 3' ends; (c) contacting the sample with an enzyme capable of initiating DNA synthesis at a nicked site, and unmethylated nucleotides, thereby generating a plurality of nucleic acid sequences comprising unmethylated nucleotides in the targeted sites of interest and wherein the nucleic acid sequences are adapter ligated on the 5' and 3' ends; and (d) contacting the sample with an enzyme capable of cutting methylated nucleic acids, thereby generating a plurality of nucleic acid fragments comprising methylated nucleic acids, wherein the plurality of nucleic acid fragments comprising methylated nucleic acids that are adapter ligated on at most one of the 5' and 3' ends. In one embodiment, the nucleic acid-guided nuclease nickase is selected from the group consisting of CAS Class I Type I nickase, CAS Class I Type III nickase, CAS Class I Type IV nickase, CAS Class II Type II nickase, and CAS Class II Type V nickase. In one embodiment the nucleic acid-guided nuclease nickase is selected from the group consisting of Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2c2 nickase, and NgAgo nickase. In one embodiment the gNAs are gRNAs. In one embodiment the gNAs are gDNAs. In one embodiment the DNA is double stranded DNA. In one embodiment the double stranded DNA is from genomic DNA. In one embodiment the genomic DNA is human. In one embodiment the DNA sequences are from 20 bp to 5000 bp in length. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment the targeted sites of interest represent less than 50% of the total DNA in the sample. In one embodiment the sample is obtained from a biological sample, a clinical sample, a forensic sample, or an environ-mental sample. In one embodiment the enzyme capable of initiating nucleic acid synthesis at a nicked site is DNA Polymerase I, Klenow fragment a TAQ polymerase, or a Bst DNA Polymerase. In one embodiment the nucleic acid-guided nuclease nickase nicks the 5' end of the DNA sequences. In one embodiment the enzyme capable of cutting methylated DNA is DpnI.

In another aspect, the invention provides a method of capturing target DNA sequences of interest comprising: (a) contacting the sample with a plurality of nucleic acid-guided nuclease nickase-gNA complexes, wherein the gNAs are complementary to targeted sites flanking a region of interest in a subset of the DNA sequences, thereby generating a plurality of nicked DNA at sites adjacent to the regions of interest (b) heating to 65° C. to cause nicks in close proximity to generate a double stranded break (c) contacting these double stranded breaks with a thermostable ligase thereby allowing ligation of adapter sequences at these sites only and (d), repeating these three steps to place a second adapter on the other side of the region of interest, thus allowing enrichment of the region of interest. In one embodiment, the gNAs are gRNAs. In one embodiment, the gNAs are gDNAs. In one embodiment, the nucleic acid-guided nuclease nickase is selected from the group consisting of CAS Class I Type I nickase, CAS Class I Type III nickase, CAS Class I Type IV nickase, CAS Class II Type II nickase, and CAS Class II Type V nickase. In one embodiment the nucleic acid-guided nuclease nickase is selected from the group consisting of Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, and NgAgo nickase. In one embodiment the DNA is double stranded DNA. In one embodiment the double stranded DNA is from genomic DNA. In one embodiment the genomic DNA is human. In one embodiment the DNA sequences are from 20 bp to 5000 bp in length. In one embodiment the targeted sites of interest are single nucleotide polymorphisms (SNPs), short tandem repeats (STRs), cancer genes, inserts, deletions, structural variations, exons, genetic mutations, or regulatory regions. In one embodiment the targeted sites of interest represent less than 50% of the total DNA in the sample. In one embodiment the sample is obtained from a biological sample, a clinical sample, a forensic sample, or an environmental sample. In one embodiment the ligase capable of contacting the double stranded break is Thermostable 5'App DNA/RNA ligase, or T4 RNA ligase. In one embodiment the nucleic acid-guided nuclease nickase nicks the 5' end of the DNA sequences. In one embodiment the enzyme capable of cutting methylated DNA is DpnI.

In another aspect, the invention provides a method of enriching a sample for sequences of interest, comprising: (a) providing a sample comprising sequences of interest and targeted sequences for depletion, wherein the sequences of interest comprise less than 50% of the sample; and (b) contacting the sample with a plurality of either nucleic acid-guided RNA endonuclease-gRNA complexes or a plurality of nucleic acid-guided DNA endonuclease-gDNA complexes, wherein the gRNAs and gDNAs are complementary to the targeted sequences, and whereby the targeted sequences are cleaved. In one embodiment, the method further comprises extracting the sequences of interest and the targeted sequences for depletion from the sample. In one embodiment, the method further comprises fragmenting the extracted sequences. In one embodiment, the cleaved targeted sequences are removed by size-exclusion. In one embodiment, the sample is any one of a biological sample, a clinical sample, a forensic sample or an environmental sample. In one embodiment, the sample comprises host nucleic acid sequences targeted for depletion and non-host nucleic acid sequences of interest. In one embodiment, the non-host nucleic acid sequences comprise microbial nucleic acid sequences. In one embodiment, the microbial nucleic acid sequences are bacterial, viral or eukaryotic parasitic nucleic acid sequences. In one embodiment, the gRNAs and gDNAs are complementary to ribosomal RNA sequences, spliced transcripts, unspliced transcripts, introns, exons, or noncoding RNAs. In one embodiment, the extracted nucleic acids include single-stranded or double-stranded RNA. In one embodiment, the extracted nucleic acids include single-stranded or double-stranded DNA. In one embodiment, the sequences of interest comprise less than 10% of the extracted nucleic acids. In one embodiment, the nucleic acid-guided RNA endonuclease comprises C2c2. In one embodiment, the C2c2 is catalytically dead. In one embodiment, the nucleic acid-guided DNA endonuclease comprises NgAgo. In one embodiment, the NgAgo is catalytically dead. In one embodiment, the sample is selected from whole blood, plasma, serum, tears, saliva, mucous, cerebrospinal fluid, teeth, bone, fingernails, feces, urine, tissue, and a biopsy.

In another aspect, the invention provides a method of enriching a sample comprising: (a) providing a sample comprising host nucleic acids and non-host nucleic acids; (b) contacting the sample with a plurality of nucleic acid-guided RNA endonuclease-gRNA complexes or a plurality of nucleic acid-guided DNA endonuclease-gDNA complexes, wherein the gRNAs and gDNAs are complementary to targeted sites in the host nucleic acids, and (c) enriching the sample for non-host nucleic acids. In one embodiment, the nucleic acid-guided RNA endonuclease comprises C2c2. In one embodiment, the nucleic acid-guided RNA endonuclease comprises catalytically dead C2c2. In one embodiment, the nucleic acid-guided DNA endonuclease comprises NgAgo. In one embodiment, the nucleic acid-guided DNA endonuclease comprises catalytically dead NgAgo. In one embodiment, the host is selected from the group consisting of a human, cow, horse, sheep, pig, monkey, dog, cat, gerbil, bird, mouse, and rat. In one embodiment, the non-host is a prokaryotic organism. In one embodiment, the non-host is selected from the group consisting of a eukaryote, a virus, a bacterium, a fungus, and a protozoan. In one embodiment, the adapter-ligated host nucleic acids and non-host nucleic acids range from 50 bp to 1000 bp in length. In one embodiment, the non-host nucleic acids comprise less than 50% of the total nucleic acids in the sample. In one embodiment, the sample is any one of a biological sample, a clinical sample, a forensic sample or an environmental sample. In one embodiment, step (c) comprises reverse-transcribing the product of step (b) into cDNA. In one embodiment, step (c) comprises removing the host nucleic acids by size-exclusion. In one embodiment, step (c) comprises removing the host nucleic acids with the use of biotin. In one embodiment, the sample is selected from whole blood, plasma, serum, tears, saliva, mucous, cerebrospinal fluid, teeth, bone, fingernails, feces, urine, tissue, and a biopsy.

In another aspect, the invention provides a method of using a nucleic acid-guided RNA endonuclease to enrich for a target in an RNA sample using labeled, catalytically dead nucleic acid-guided RNA endonuclease protein. In some embodiments, the nucleic acid-guided RNA endonuclease protein is targeted to HIV RNA in a blood RNA sample, and host RNA is washed away. In some embodiments, nucleic acid-guided RNA endonuclease is C2c2.

In another aspect, the invention provides a composition comprising a nucleic acid fragment, a nucleic acid-guided nuclease nickase-gNA complex, and labeled nucleotides. In one embodiment, the nucleic acid comprises DNA. In one embodiment, the nucleic acid-guided nuclease nickase is selected from the group consisting of CAS Class I Type I nickase, CAS Class I Type III nickase, CAS Class I Type IV nickase, CAS Class II Type II nickase, and CAS Class II Type V nickase. In one embodiment, the nucleic acid-guided nuclease nickase is selected from the group consisting of Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, and NgAgo nickase. In one embodiment, the gNAs are gRNAs. In one embodiment, the gNAs are gDNAs. In one embodiment, the nucleic acid fragment comprises DNA. In one embodiment, the nucleic acid fragment comprises RNA. In one embodiment, the nucleotides are labeled with biotin. In one embodiment, the nucleotides are part of an antibody conjugate pair.

In another aspect, the invention provides a composition comprising a nucleic acid fragment and a catalytically dead nucleic acid-guided nuclease-gNA complex, wherein the catalytically dead nucleic acid-guided nuclease is fused to a transposase. In one embodiment, the catalytically-dead nucleic acid-guided nuclease is selected from the group consisting of dead CAS Class I Type I, dead CAS Class I Type III, dead CAS Class I Type IV, dead CAS Class II Type II, and dead CAS Class II Type V. In one embodiment, the catalytically dead nucleic acid-guided nuclease is selected from the group consisting of dCas9, dCpf1, dCas3, dCas8a-c, dCas10, dCse1, dCsy1, dCsn2, dCas4, dCsm2, dCm5, dCsf1, dC2C2, and dNgAgo. In one embodiment, the gNAs are gRNAs. In one embodiment, the gNAs are gDNAs. In one embodiment, the nucleic acid fragment comprises DNA. In one embodiment, the nucleic acid fragment comprises RNA. In one embodiment, the catalytically dead nucleic acid-guided nuclease is fused to the N-terminus of the transposase. In one embodiment, the catalytically dead nucleic acid-guided nuclease is fused to the C-terminus of the transposase. In one embodiment, the composition comprises a DNA fragment and a dCas9-gRNA complex, wherein the dCas9 is fused to a transposase.

In another aspect, the invention provides a composition comprising a nucleic acid fragment comprising methylated nucleotides, a nucleic acid-guided nuclease nickase-gNA complex, and unmethylated nucleotides. In one embodiment, the nucleic acid-guided nuclease nickase is selected from the group consisting of CAS Class I Type I nickase, CAS Class I Type III nickase, CAS Class I Type IV nickase, CAS Class II Type II nickase, and CAS Class II Type V nickase. In one embodiment, the nucleic acid-guided nuclease nickase is selected from the group consisting of Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, and NgAgo nickase. In one embodiment, the gNAs are gRNAs. In one embodiment, the gNAs are gDNAs. In one embodiment, the nucleic acid fragment comprises DNA. In one embodiment, the nucleic acid fragment comprises RNA. In one embodiment, the nucleotides are labeled with biotin. In one embodiment, the nucleotides are part of an antibody conjugate pair. In one embodiment, the composition comprises a DNA fragment comprising methylated nucleotides, a nickase Cas9-gRNA complex, and unmethylated nucleotides.

DETAILED DESCRIPTION OF THE INVENTION

Definitions

Figure 1:
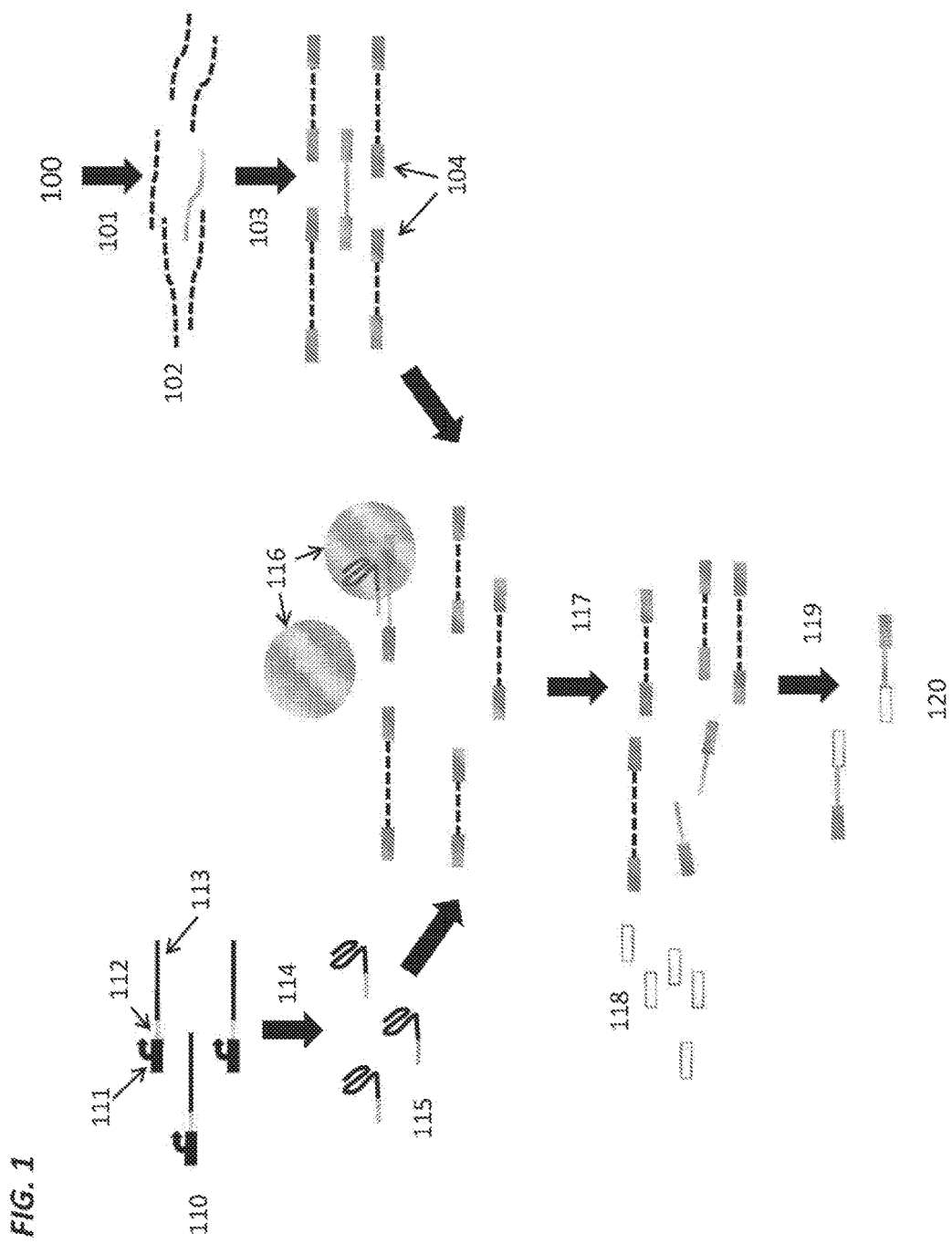
FIG. 1 illustrates a first protocol for the capture of target nucleic acids from a library of human genomic DNA.
Figure 2:
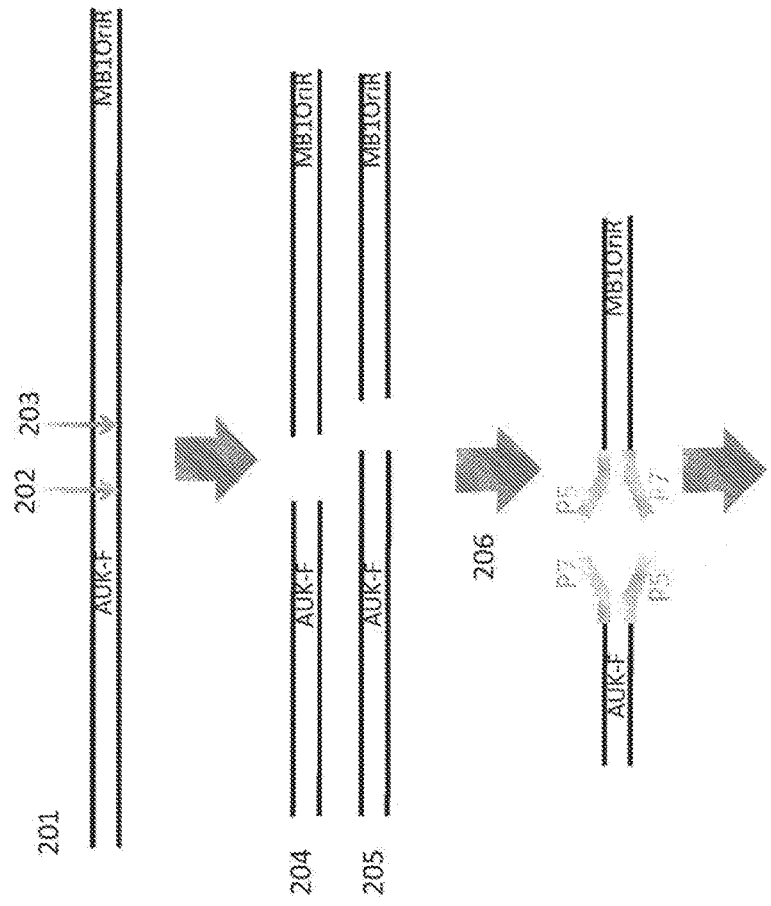
FIG. 2 further illustrates the protocol for the capture of target nucleic acids (e.g. DNA) from a nucleic acid mixture. Target nucleic acid is cut with a nucleic acid-guided nuclease, following which adapters are ligated into the newly available blunt ends.
Figure 3:
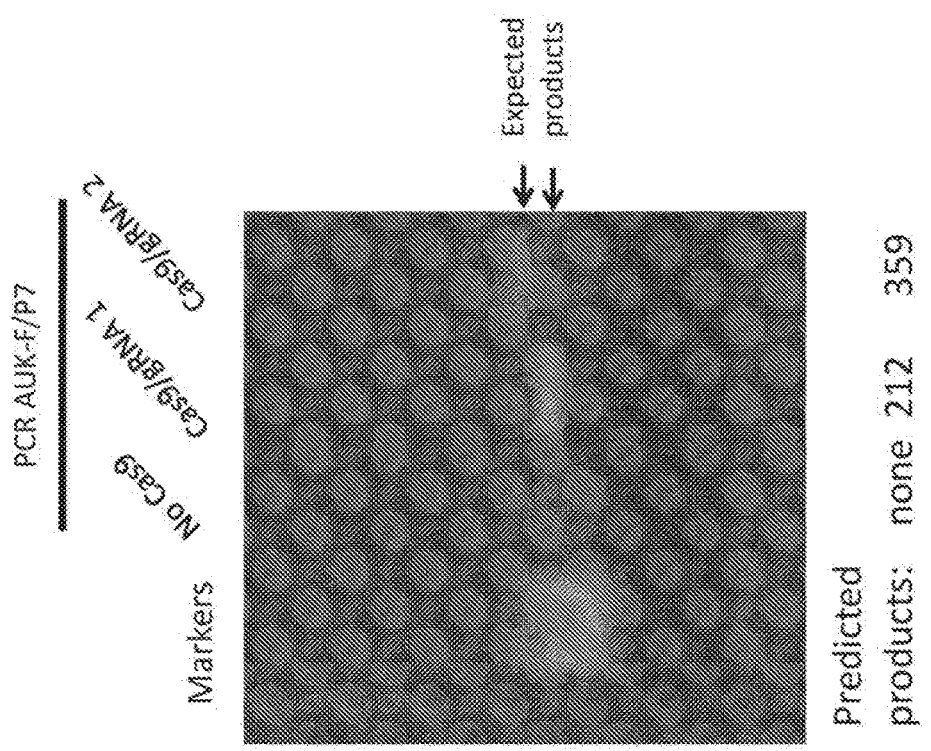
FIG. 3 illustrates that Cas9 cutting, followed by ligation of adapters, allows for specific amplification of target DNA.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

Numeric ranges are inclusive of the numbers defining the range.

The term "sample" as used herein relates to a material or mixture of materials, typically, although not necessarily, in liquid form, containing one or more analytes of interest.

The term "nucleic acid sample," as used herein denotes a sample containing nucleic acids. Nucleic acid samples used herein may be complex in that they contain multiple different molecules that contain sequences. Genomic DNA from a mammal is a type of a complex sample. Complex samples may have more then $10^4$, $10^5$, $10^6$ or $10^7$ different nucleic acid molecules. A DNA target may originate from any source such as genomic DNA, cDNA, or an artificial DNA construct. Any sample containing nucleic acid, e.g., genomic DNA made from tissue culture cells or a sample of tissue, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acids" and "polynucleotides" are used interchangeably herein. Polynucleotide is used to describe a nucleic acid polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbones, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides.

Unless otherwise indicated, nucleic acids are written left to right in 5' to 3' orientation; amino acid sequences are written left to right in amino to carboxy orientation, respectively.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "cleavage site, as used herein, refers to the site at which a double-stranded DNA molecule has been cleaved.

The "nucleic acid-guided nuclease-gNA complex" refers to a complex comprising a nucleic acid-guided nuclease protein and a guide nucleic acid (gNA, for example a gRNA or a gDNA). For example the "Cas9-gRNA complex" refers to a complex comprising a Cas9 protein and a guide RNA (gRNA). The nucleic acid-guided nuclease may be any type of nucleic acid-guided nuclease, including but not limited to wild type nucleic acid-guided nuclease, a catalytically dead nucleic acid-guided nuclease, or a nucleic acid-guided nuclease-nickase.

The term "nucleic acid-guided nuclease-associated guide NA" refers to a guide nucleic acid (guide NA). The nucleic acid-guided nuclease-associated guide NA may exist as an isolated nucleic acid, or as part of a nucleic acid-guided nuclease-gNA complex, for example a Cas9-gRNA complex.

The terms "capture" and "enrichment" are used interchangeably herein, and refer to the process of selectively isolating a nucleic acid region containing: sequences of interest, targeted sites of interest, sequences not of interest, or targeted sites not of interest.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example.

The term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment," as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adapter ligated (in which case it has an adapter ligated to one or both ends of the fragment, or to at least the 5' end of a molecule), or may not be adapter ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

The term "ligating," as used herein, refers to the enzymatically catalyzed joining of the terminal nucleotide at the 5' end of a first DNA molecule to the terminal nucleotide at the 3' end of a second DNA molecule.

If two nucleic acids are "complementary," each base of one of the nucleic acids base pairs with corresponding nucleotides in the other nucleic acid. The term "complementary" and "perfectly complementary" are used synonymously herein.

The term "separating," as used herein, refers to physical separation of two elements (e.g., by size or affinity, etc.) as well as degradation of one element, leaving the other intact. For example, size exclusion can be employed to separate nucleic acids, including cleaved targeted sequences.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double-stranded nucleic acid in which the top and bottom strands have been covalently linked will still be described as the "top" and "bottom" strands. In other words, for the purposes of this disclosure, the top and bottom strands of a double-stranded DNA do not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double-stranded DNA, the oligonucleotide may have two regions, a first region that hybridizes with the top strand of the double-stranded DNA, and a second region that hybridizes with the bottom strand of the double-stranded DNA.

The term "double-stranded DNA molecule" refers to both double-stranded DNA molecules in which the top and bottom strands are not covalently linked, as well as double-stranded DNA molecules in which the top and bottom stands are covalently linked. The top and bottom strands of a double-stranded DNA are base paired with one other by Watson-Crick interactions.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the $T_m$ of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acid may also be denatured chemically (e.g., using urea or NaOH).

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of consecutive nucleotides of a polynucleotide are obtained.

The term "next-generation sequencing" refers to the so-called parallelized sequencing-by-synthesis or sequencing-by-ligation platforms, for example, those currently employed by Illumina, Life Technologies, and Roche, etc. Next-generation sequencing methods may also include nanopore sequencing methods or electronic-detection based methods such as Ion Torrent technology commercialized by Life Technologies.

The term "complementary DNA" or cDNA refers to a double-stranded DNA sample that was produced from an RNA sample by reverse transcription of RNA (using primers such as random hexamers or oligo-dT primers) followed by second-strand synthesis by digestion of the RNA with RNaseH and synthesis by DNA polymerase.

The term "RNA promoter adapter" is an adapter that contains a promoter for a bacteriophage RNA polymerase, e.g., the RNA polymerase from bacteriophage T3, T7, SP6 or the like.

Other definitions of terms may appear throughout the specification.

Exemplary Methods of the Invention

As described herein, the invention provides exemplary protocols for the capture of nucleic acids and compositions for use in these protocols. Exemplary protocols are illustrated in FIGS. 1, 6, 9, 10, 11, and 13, respectively, and in the Examples section. Various uses are contemplated throughout. Specific terms referred to in this section are described in greater detail in subsequent sections.

In one embodiment, the invention provides a capture method (depicted as Protocol 1) as provided in FIGS. 1-5. In this embodiment, the method is used to capture target nucleic acid sequences. Referring to FIG. 1, the method comprises providing a sample or a library 100, subject to extraction protocols 101 (e.g. DNA extraction protocols), resulting in a sample 102 comprising >99% non-target sequence and <1% target sequence. The sample is subjected to library construction protocols 103, resulting in a nucleic acid library comprising sequencing indexed adapters 104, resulting in a plurality of adapter-ligated nucleic acids, wherein the nucleic acids are ligated to a first adapter at one end, and a second adapter at the other end. To produce a library of target-specific guide NAs (e.g. gRNAs), a library of target specific gNA precursors 110, each comprising a RNA polymerase promoter 111, a specific-base pair region 112 (e.g. a 20 base pair region), and a stem-loop binding site for a nucleic acid-guided nuclease 113, was subjected to in vitro transcription 114, yielding a library of target-specific guide RNAs 115. The library of target-specific guide NAs was then combined with nucleic acid-guided nuclease proteins 116 to yield a library of nucleic acid-guided nuclease-gNA complexes. The nucleic acid-guided nuclease-gNA complexes were then combined with the nucleic acid library such that the nucleic acid-guided nuclease cleaved matching target nucleic acid sequences and left other nucleic acids uncleaved 117. Second adapters 118 were added and allowed to ligate specifically to the 5' phosphorylated blunt ends of cleaved nucleic acids 119. This allows for downstream applications, for example amplifying the nucleic acid fragments comprising a first or second adapter at one end and a third adapter at the other end, using adapter-specific PCR 120.

In an exemplary depiction of Protocol 1, referring to FIG. 1, the method is used to capture target nucleic acid sequences. The method comprises providing a sample or a library comprising a plurality of adapter-ligated nucleic acids, wherein the nucleic acids are ligated to a first adapter at one end, and a second adapter at the other end. This is followed by contacting the sample with a plurality of Cas9-gRNA complexes, wherein the gRNAs are complementary to targeted sites of interest contained in a subset of the nucleic acids. The contacting cleaves the targeted sites of interest, thereby generating a plurality of nucleic acid fragments ligated to a first or second adapter at one end and no adapter at the other end. This step is followed by ligating the plurality of resulting nucleic acid fragments with third adapters, thereby generating a plurality of nucleic acid fragments ligated to a first or second adapter at one end and a third adapter at the other end. This allows for downstream applications, for example amplifying the nucleic acid fragments comprising a first or second adapter at one end and a third adapter at the other end, using adapter-specific PCR.

Figure 6:
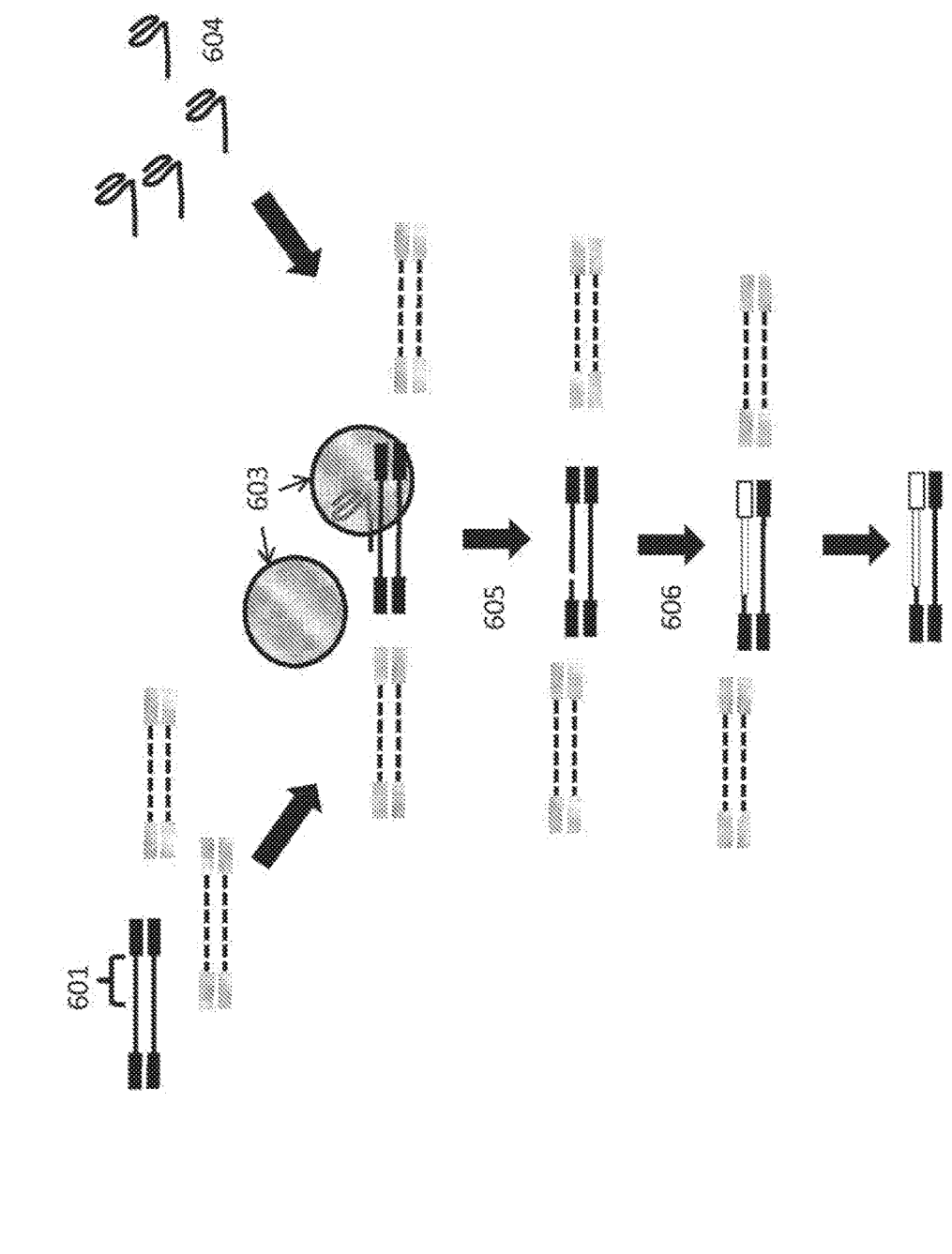
FIG. 6 illustrates a second protocol for capture: the use of a nucleic acid-guided nuclease nickase to label target nucleic acids (e.g. DNA), allowing for further capture and purification.
Figure 7:
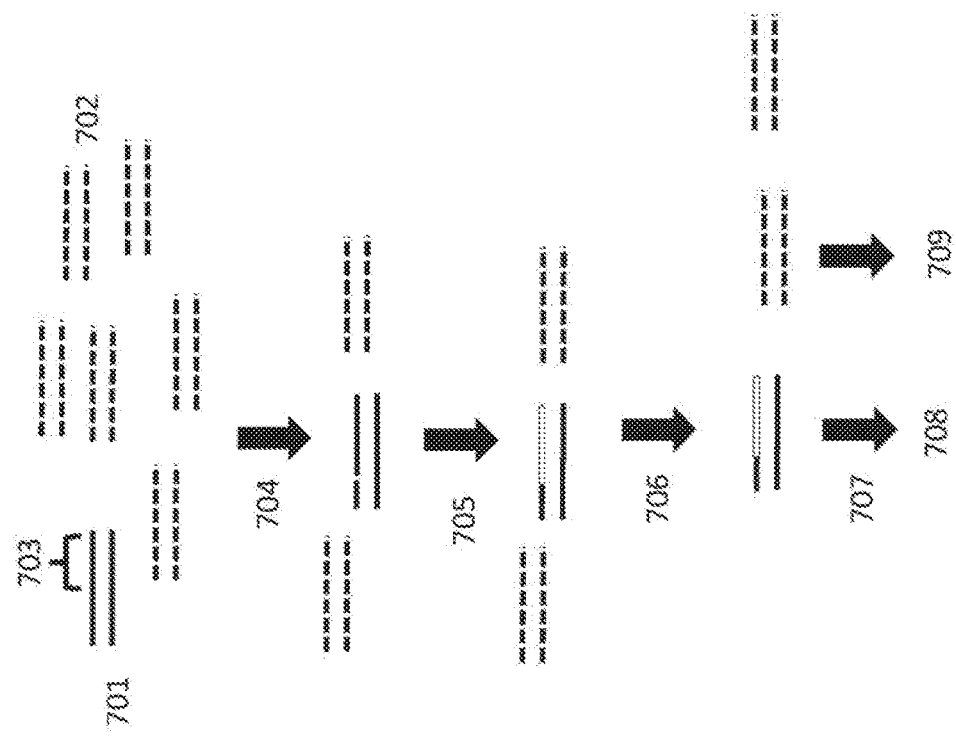
FIG. 7 illustrates a proof of principle experiment using a restriction nickase as a substitute for the nucleic acid-guided nuclease nickase.
Figure 8:
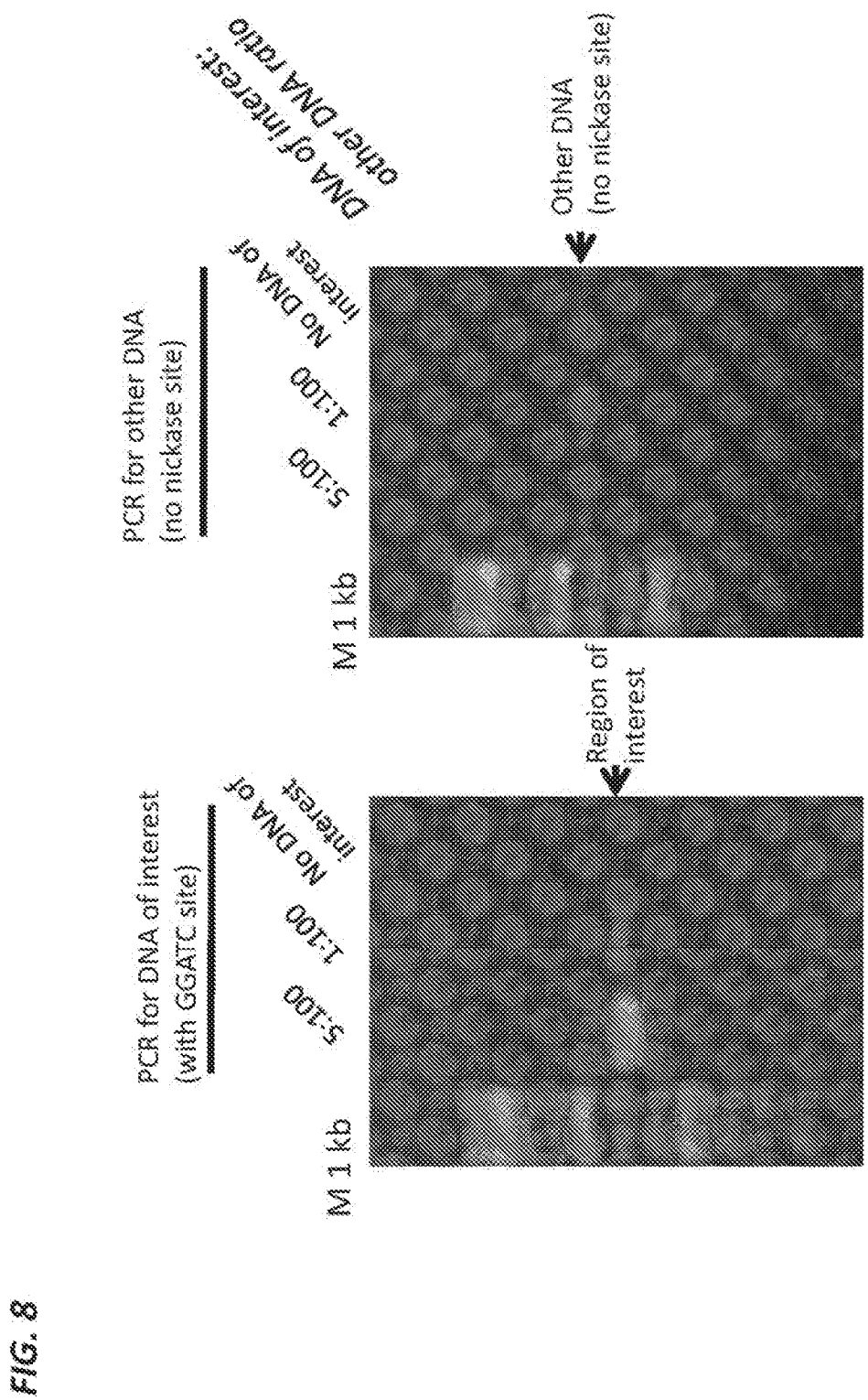
FIG. 8 illustrates that enrichment of test DNA by approximately 50-fold for the experiment illustrated in FIG. 7 (using a Cas9-nickase).

In one embodiment, the invention provides a capture method (depicted as Protocol 2) as provided in FIGS. 6-8. In this embodiment, the method is used to introduce labeled nucleotides at targeted sites of interest. The method comprises providing a sample comprising a plurality of double stranded nucleic acid fragments 601 (e.g. double stranded DNA); contacting the sample with a plurality of nucleic acid-guided nuclease nickase-gNA complexes. The nickase nucleic acid-guided nuclease 603 is guided by target-specific guide NAs 604, wherein the gNAs are complementary to targeted sites of interest in the nucleic acid fragments, thereby generating a plurality of nicked nucleic acid fragments at the targeted sites of interest. Nickase is used to nick target sequences 605. The nickase-nucleic acid-guided nuclease cleaves at target sequence. Single strand cuts (nicks) are a substrate for DNA polymerase I which can be used to replace DNA downstream of the nick with biotin labeled DNA 606.

In an exemplary depiction of Protocol 2, referring to FIG. 6, the method is used to introduce labeled nucleotides at targeted sites of interest. The method comprises providing a sample comprising a plurality of nucleic acid fragments; contacting the sample with a plurality of Cas9 nickase-gRNA complexes, wherein the gRNAs are complementary to targeted sites of interest in the nucleic acid fragments, thereby generating a plurality of nicked nucleic acid fragments at the targeted sites of interest; and then is followed by contacting the plurality of nicked nucleic acid fragments with an enzyme capable of initiating nucleic acid synthesis at a nicked site, and labeled nucleotides, thereby generating a plurality of nucleic acid fragments comprising labeled nucleotides in the targeted sites of interest.

Figure 9:
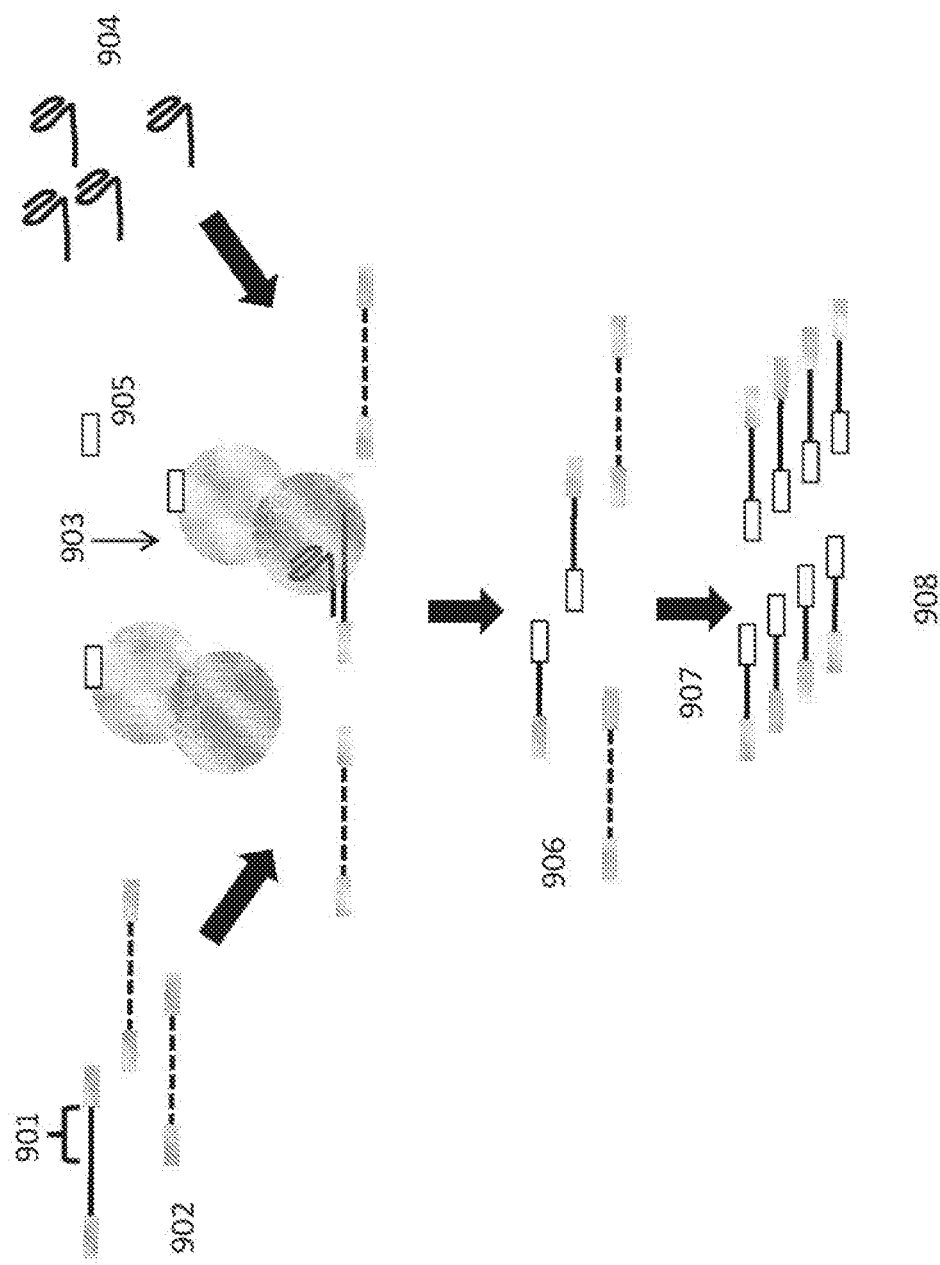
FIG. 9 illustrates a third protocol for capture: the use of a catalytically dead nucleic acid-guided nuclease-transposase fusion to insert adaptors in human genomic library, to allowing for enrichment of specific SNPs.

In one embodiment, the invention provides a capture method (depicted as Protocol 3) as provided in FIG. 9. In this embodiment, the method is used to capture target nucleic acid sequences of interest 901. The method first involves providing a sample comprising a plurality of adapter-ligated nucleic acids 902, wherein the nucleic acids are ligated to a first adapter at one end and are ligated to a second adapter at the other end. This is then followed by contacting the sample with a plurality of catalytically dead nucleic acid-guided nuclease-gNA complexes, wherein the catalytically dead nucleic acid-guided nuclease is fused to a transposase 903, wherein the gNAs 904 are complementary to targeted sites of interest contained in a subset of the nucleic acids, and wherein the catalytically dead nucleic acid-guided nuclease-gNA transposase complexes are loaded with a plurality of third adapters 905, to generate a plurality of nucleic acids fragments 906 comprising either a first or second adapter at one end and a third adapter at the other end. These fragments can then be amplified 907 using the adapter sequences and then sequenced 908.

In an exemplary depiction of Protocol 3, referring to FIG. 9, the method is used to capture target nucleic acid sequences of interest. The method first involves providing a sample comprising a plurality of adapter-ligated nucleic acids, wherein the nucleic acids are ligated to a first adapter at one end and are ligated to a second adapter at the other end. This is then followed by contacting the sample with a plurality of dCas9-gRNA complexes, wherein the dCas9 is fused to a transposase, wherein the gRNAs are complementary to targeted sites of interest contained in a subset of the nucleic acids, and wherein the dCas9-gRNA transposase complexes are loaded with a plurality of third adapters, to generate a plurality of nucleic acids fragments comprising either a first or second adapter at one end and a third adapter at the other end.

Figure 10:
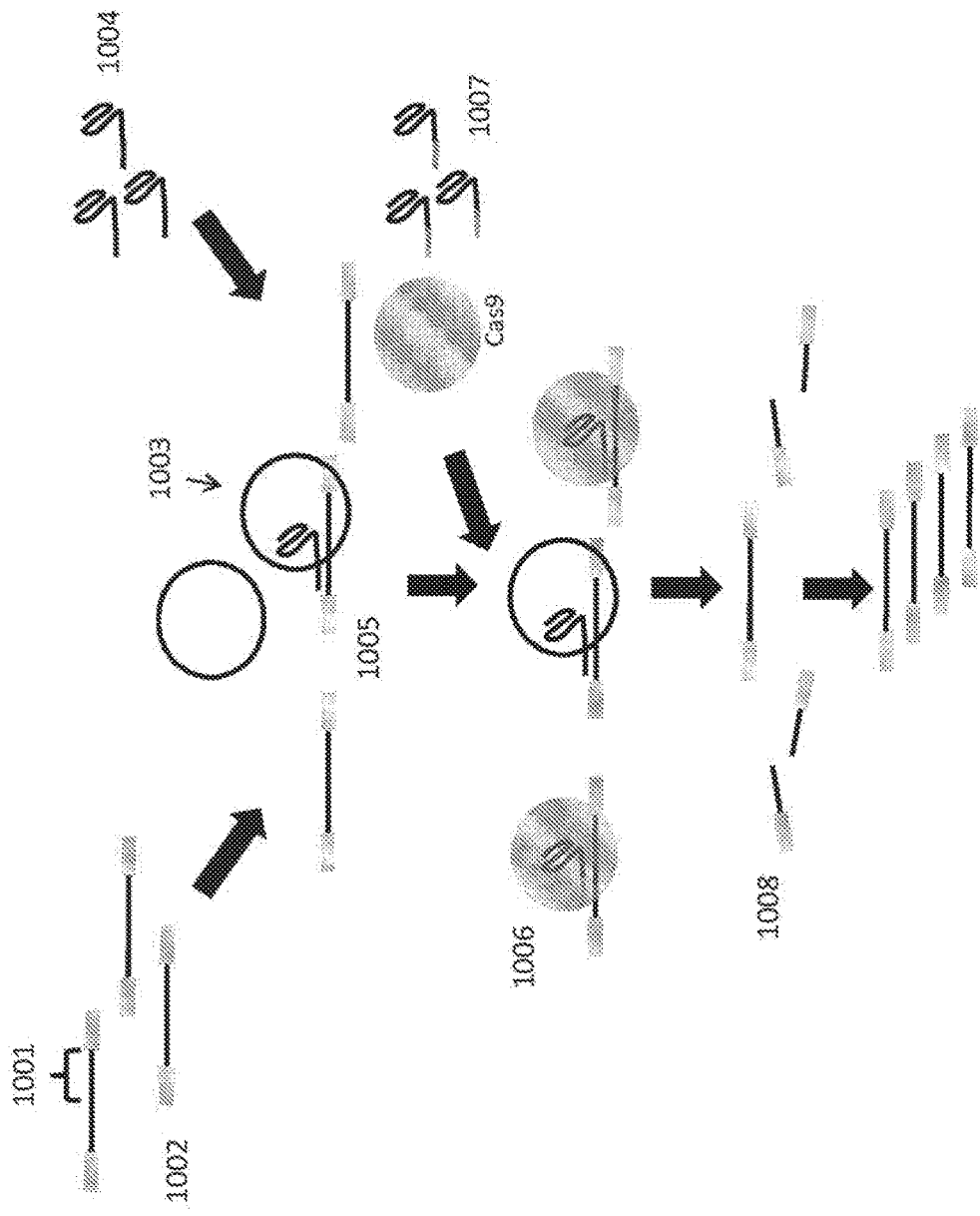
FIG. 10 illustrates a fourth protocol for capture: the use of dead nucleic acid-guided nuclease to protect targeted sites from subsequent fragmentation by a nucleic acid-guided nuclease, allowing for enrichment of regions of interest.

In one embodiment, the invention provides a capture method (depicted as Protocol 4) as provided for example in FIG. 10. In this embodiment, the method is used to capture target nucleic acid sequences of interest 1001. The method comprises first providing a sample comprising a plurality of adapter-ligated nucleic acids 1002, wherein the nucleic acids are ligated to the adapter at the 5' end and 3' ends. The method then involves contacting the sample with a plurality of catalytically dead nucleic acid-guided nuclease-gNA complexes 1003, wherein the gNAs 1004 are complementary to targeted sites of interest contained in a subset of the nucleic acids, thereby generating a plurality of nucleic acids adapter-ligated at the 5' and 3' ends, bound to a catalytically dead nucleic acid-guided nuclease-gNA complex 1005. This is followed by contacting the sample with a plurality of nucleic acid-guided nuclease-gNA complexes 1006, wherein the gNAs 1007 are complementary to targeted sites of interest and targeted sites not of interest in the nucleic acids, thereby generating a plurality of nucleic acid fragments 1008 comprising nucleic acid sequences not of interest, adapter ligated at only one of the 5' or 3' ends. In this method wherein the second contacting step, contacting with a plurality of nucleic acid-guided nuclease-gNA complexes, does not displace the plurality of nucleic acids adapter-ligated at the 5' and 3' ends, bound to a catalytically dead nucleic acid-guided nuclease-gNA complex of step (b).

In an exemplary depiction of Protocol 4, referring to FIG. 10, the method is used to capture target nucleic acid sequences of interest. The method comprises first providing a sample comprising a plurality of adapter-ligated nucleic acids, wherein the nucleic acids are ligated to the adapter at the 5' end and 3' ends. The method then involves contacting the sample with a plurality of dead nucleic acid-guided nuclease-gNA complexes (e.g., dCas9-gRNA) complexes, wherein the gNAs are complementary to targeted sites of interest contained in a subset of the nucleic acids, thereby generating a plurality of nucleic acids adapter-ligated at the 5' and 3' ends, bound to a dead nucleic acid-guided nuclease-gNA complex (e.g., dCAS9-gRNA complex). This is followed by contacting the sample with a plurality of nucleic acid-guided nuclease-gNA complexes (e.g., Cas9-gRNA complexes), wherein the gNAs are complementary to targeted sites of interest and targeted sites not of interest in the nucleic acids, thereby generating a plurality of nucleic acid fragments comprising nucleic acid sequences not of interest, adapter ligated at only one of the 5' or 3' ends. In this method wherein the second contacting step, contacting with a plurality of nucleic acid-guided nuclease-gNA complexes (e.g., Cas9-gRNA complexes), does not displace the plurality of nucleic acids adapter-ligated at the 5' and 3' ends, bound to a dead nucleic acid-guided nuclease-gNA complex (e.g., dCAS9-gRNA complex) of step (b).

Figure 11:
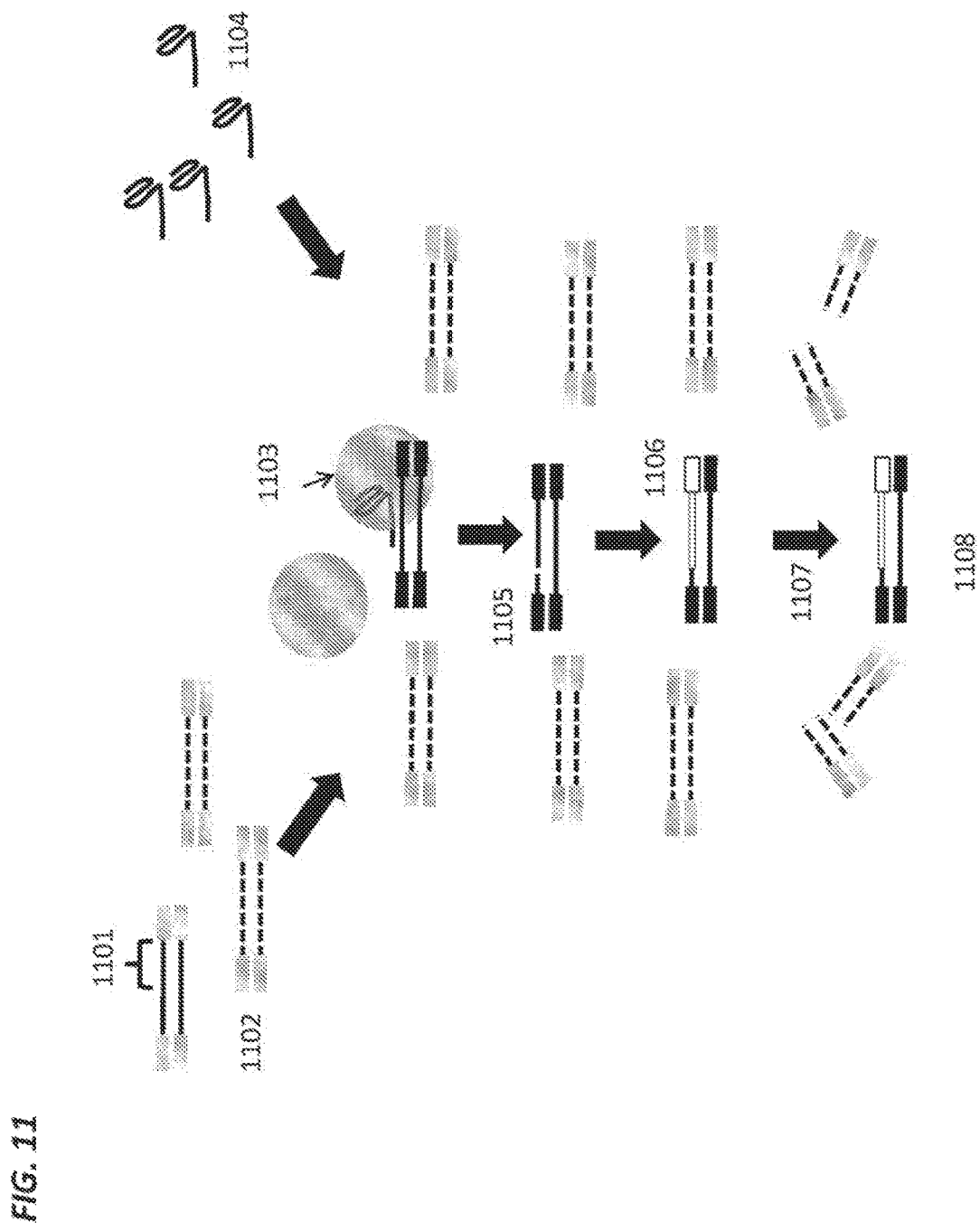
FIG. 11 illustrates a fifth protocol for capture: the use of a nucleic acid-guided nuclease nickase to protect and then enrich any targeted region, for example SNPs or STRs, from, for example, human genomic DNA, by replacing methylated DNA with unmethylated DNA.
Figure 12:
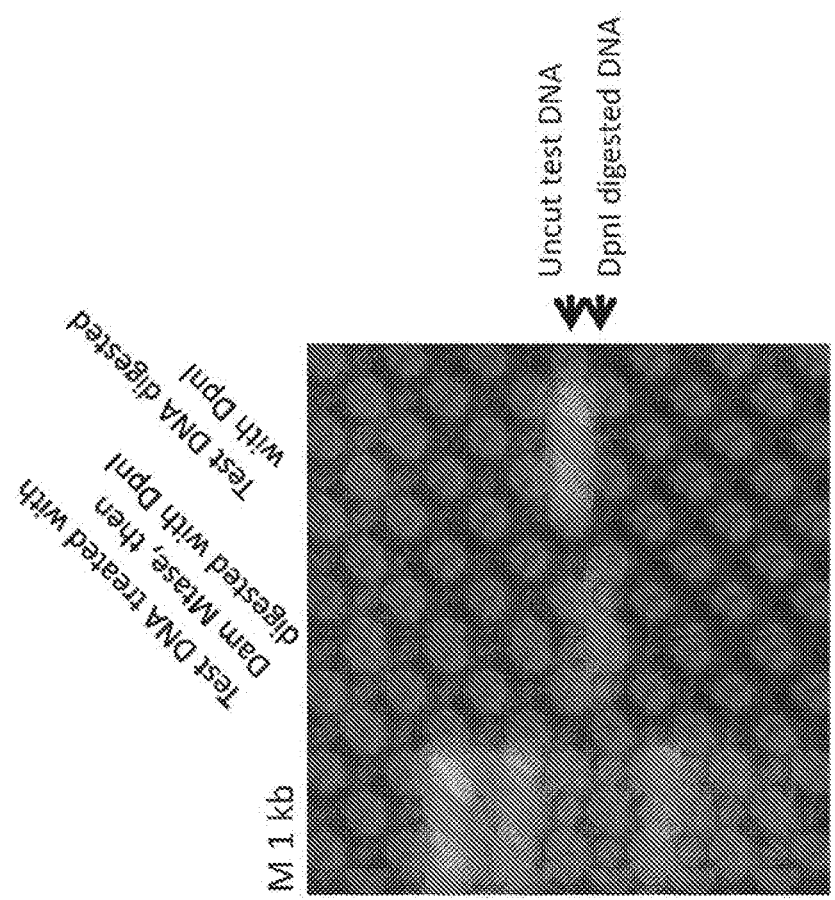
FIG. 12 illustrates that the methylation of test DNA in the fifth protocol renders it susceptible to DpnI-mediated cleavage.

In one embodiment, the invention provides a capture method (depicted as Protocol 5) as provided, for example, in FIG. 11 and FIG. 12. In this embodiment, the method is used to capture target nucleic sequences of interest 1101. The method involves first providing a sample comprising a plurality of sequences 1102, wherein the sequences comprise methylated nucleotides (e.g., treated with Dam methyltransferase), and wherein the sequences are adapter ligated on the 5' and 3' ends. The method then involves first contacting the sample with a plurality of nucleic acid-guided nuclease nickase-gNA complexes 1103, wherein the gNAs 1104 are complementary to targeted sites of interest in a subset of the sequences, thereby generating a plurality of nicked nucleic acid sequences 1105 at the targeted sites of interest, and wherein the nucleic acid sequences are adapter ligated on the 5' and 3' ends. Where the nucleic acid is DNA, single strand cuts (nicks) can be, for example, a substrate for DNA polymerase I, which replaces the DNA downstream of the nick with unmethylated DNA. This can then be followed by then contacting the sample with an enzyme capable of initiating DNA synthesis at a nicked site, and unmethylated nucleotides, thereby generating a plurality of DNA comprising unmethylated nucleotides 1106 in the targeted sites of interest and wherein the DNA sequences are adapter ligated on the 5' and 3' ends. This is then followed by contacting the sample with an enzyme capable of cutting methylated DNA (e.g., DpnI) 1107, thereby generating a plurality of DNA fragments comprising methylated DNA, wherein the plurality of DNA fragments comprising methylated DNA are adapter ligated only one of the 5' and 3' ends. Remaining intact nucleic acid can be amplified and sequenced 1108. FIG. 12 shows, for example, results from an experiment conducted according to this protocol. The first column on the gel shows a 1 kb ladder, the second column shows test DNA treated with Dam methyltransferase, then digested with DpnI, and the third column shows test DNA digested with DpnI. The second column shows a band corresponding to DpnI digested DNA, while the third column shows a band corresponding to uncut test DNA.

In an exemplary depiction of Protocol 5, referring to FIGS. 11-12, the method is used to capture target DNA sequences of interest. The method involves first providing a sample comprising a plurality of DNA sequences, wherein the DNA sequences comprise methylated nucleotides, and wherein the DNA sequences are adapter ligated on the 5' and 3' ends. The method then involves first contacting the sample with a plurality of Cas9 nickase-gRNA complexes, wherein the gRNAs are complementary to targeted sites of interest in a subset of the DNA sequences, thereby generating a plurality of nicked DNA at the targeted sites of interest, and wherein the DNA are adapter ligated on the 5' and 3' ends. This is then followed by then contacting the sample with an enzyme capable of initiating DNA synthesis at a nicked site, and unmethylated nucleotides, thereby generating a plurality of DNA comprising unmethylated nucleotides in the targeted sites of interest and wherein the DNA sequences are adapter ligated on the 5' and 3' ends. This is then followed by contacting the sample with an enzyme capable of cutting methylated DNA, thereby generating a plurality of DNA fragments comprising methylated DNA, wherein the plurality of DNA fragments comprising methylated DNA are adapter ligated only one of the 5' and 3' ends.

Figure 13:
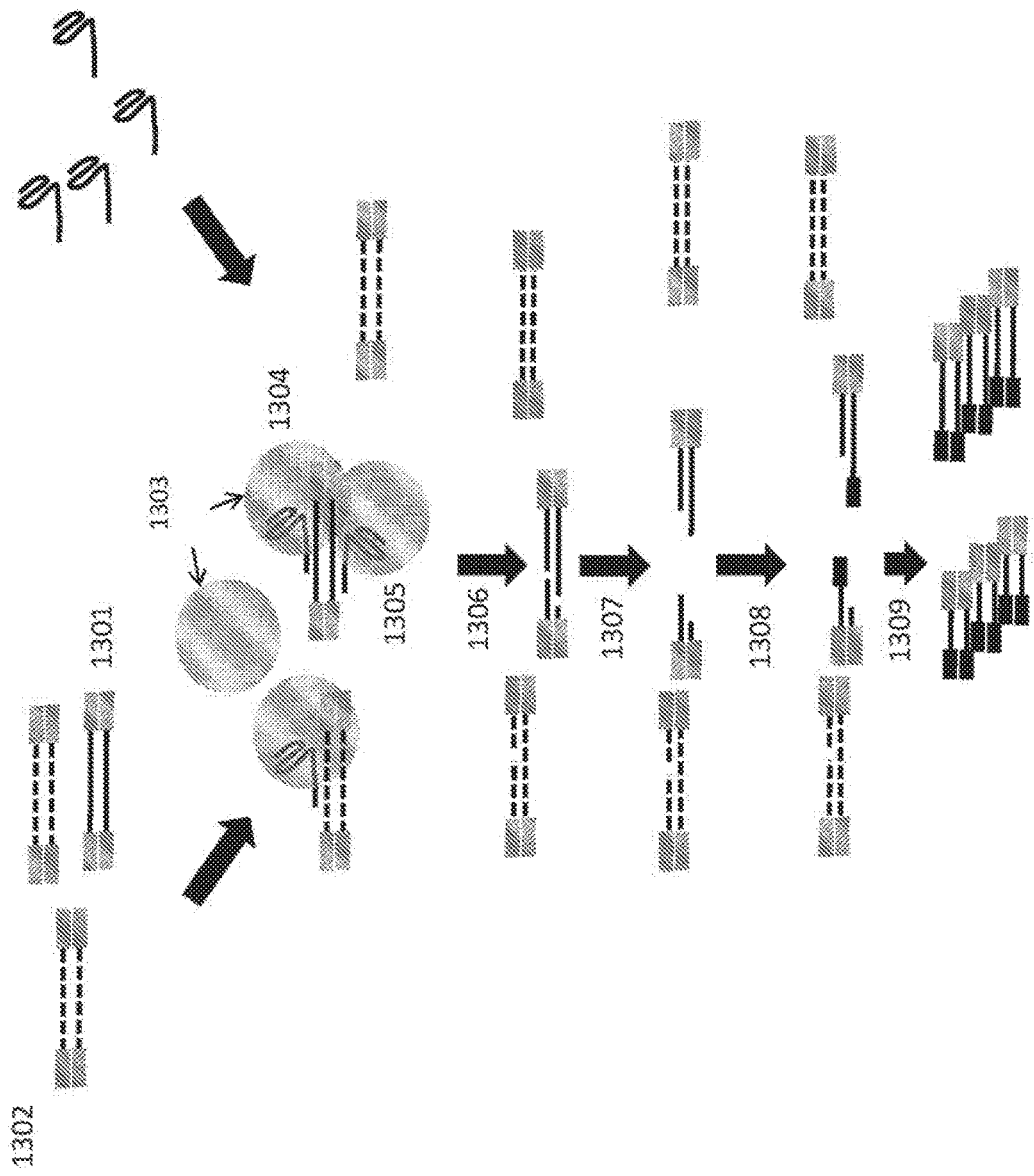
FIG. 13 illustrates a sixth protocol for capture: the use of a nucleic acid-guided nuclease nickase to introduce two double stranded breaks delineating a region of interest, allowing for 3' single stranded ligation of adapters and subsequent enrichment.

In one embodiment, the invention provides a capture method (depicted as Protocol 6) as provided in FIG. 13. The objective of this method is to enrich a region of a nucleic acid 1301, from any source (e.g., library 1302, genomic, or PCR), as depicted for example in FIG. 13. The nucleic acid-guided nuclease—nickase 1303 can be targeted to proximal sites using two guide NAs 1304 and 1305, resulting in nicking of nucleic acid at each location 1306. Alternatively, an adapter can be ligated on only one side, then filled in, then an adapter can be ligated on the other side. The two nicks can be close to each other (e.g., within 10 to 15 bp). Single nicks may be generated in non-target molecules. Because of the proximity of the two nicking sites, a double stranded break can be created when the reaction is heated 1307, e.g. to 65° C., resulting in long (e.g., 10-15 bp) 3' overhangs. These overhangs can be recognized by a thermostable single stranded DNA/RNA ligase, to allow for site-specific ligation 1308 of single stranded adapters. The ligase can, for example, only recognize long 3' overhangs, thus ensuring that adapters will not be ligated at other sites. This process can be repeated using nucleic acid-guided nuclease nickase and guide NAs targeting on the other side of the region of interest, followed by ligation as above using a second single stranded adapter. Once two adapters have been ligated on either side of the region of interest, the region can be amplified or sequenced directly 1309.

In an exemplary depiction of Protocol 6, referring to FIG. 13, the method is to enrich a region of DNA, from any DNA source (e.g., library, genomic, or PCR). A Cas9 Nickase can be targeted to proximal sites using two guide RNAs and, resulting in nicking of DNA at each location. Alternatively, an adapter can be ligated on only one side, then filled in, then an adapter can be ligated on the other side. The two nicks can be close to each other (e.g., within 10 to 15 bp). Single nicks may be generated in non-target molecules. Because of the proximity of the two nicking sites, a double stranded break can be created when the reaction is heated, e.g. to 65° C., resulting in long (e.g., 10-15 bp) 3' overhangs. These overhangs can be recognized by a thermostable single stranded DNA/RNA ligase, such as a Thermostable 5'App DNA/RNA ligase to allow for site-specific ligation of single stranded adapters. The ligase can, for example, only recognize long 3' overhangs, thus ensuring that adapters will not be ligated at other sites. This process can be repeated using Cas9 Nickase and guide RNA targeting on the other side of the region of interest, followed by ligation as above using a second single stranded adapter. Once two adapters have been ligated on either side of the region of interest, the region can be amplified or sequenced directly.

In one embodiment, provided herein is a method of enriching a sample for sequences of interest, comprising: (a) providing a sample comprising sequences of interest and targeted sequences for depletion, wherein the sequences of interest comprise less than 50% of the sample; and (b) contacting the sample with a plurality of nucleic acid-guided RNA endonuclease-gRNA complexes or a plurality of nucleic acid-guided DNA endonuclease-gDNA complexes, wherein the gRNAs and gDNAs are complementary to the targeted sequences. In some embodiments, the targeted sequences are thereby cleaved. In one embodiment, the nucleic acid-guided RNA endonuclease is C2c2. In one embodiment the C2c2 is catalytically dead. In one embodiment, the nucleic acid-guided DNA endonuclease is NgAgo (Argonaute from *Natronobacterium gregoryi*). In one embodiment the NgAgo is catalytically dead.

In one embodiment, provided herein is a method of enriching a sample comprising: (a) providing a sample comprising host nucleic acids and non-host nucleic acids; (b) contacting the sample with a plurality of nucleic acid-guided RNA endonuclease-gRNA complexes or plurality of nucleic acid-guided DNA endonuclease-gDNA complexes, wherein the gNAs are complementary to targeted sites in the host nucleic acids, and (c) enriching the sample for non-host nucleic acids. In one embodiment, the nucleic acid-guided RNA endonuclease is C2c2. In one embodiment the C2c2 is catalytically dead. In one embodiment, the nucleic acid-guided DNA endonuclease is NgAgo. In one embodiment the NgAgo is catalytically dead.

Nucleic Acids, Samples

Nucleic acids of the invention (targeted for capture) can be any DNA, any RNA, single stranded DNA, single stranded RNA, double stranded DNA, double stranded RNA, artificial DNA, artificial RNA, synthetic DNA, synthetic RNA, and RNA/DNA hybrids.

The nucleic acids of the invention can be a genomic fragment, comprising a region of the genome, or the whole genome itself. In one embodiment, the genome is a DNA genome. In another embodiment, the genome is a RNA genome.

Nucleic acids of the invention can be obtained from a eukaryotic or prokaryotic organism; from a mammalian organism or a non-mammalian organism; from an animal or a plant; from a bacteria or virus; from an animal parasite; or from a pathogen.

Nucleic acids of the invention can be obtained from any mammalian organism. In one embodiment the mammal is a human. In another embodiment the mammal is a livestock animal, for example a horse, a sheep, a cow, a pig, or a donkey. In another embodiment, a mammalian organism is a domestic pet, for example a cat, a dog, a gerbil, a mouse, a rat. In another embodiment the mammal is a type of a monkey.

Nucleic acids of the invention can be obtained from any bird or avian organism. An avian organism includes but is not limited to chicken, turkey, duck and goose.

Nucleic acids of the invention can be obtained from a plant. In one embodiment, the plant is rice, maize, wheat, rose, grape, coffee, fruit, tomato, potato, or cotton.

In some embodiments, nucleic acids of the invention are obtained from a species of bacteria. In one embodiment, the bacteria are tuberculosis-causing bacteria.

In some embodiments, nucleic acids of the invention are obtained from a virus.

In some embodiments, nucleic acids of the invention are obtained from a species of fungi.

In some embodiments, nucleic acids of the invention are obtained from a species of algae.

In some embodiments, nucleic acids of the invention are obtained from any mammalian parasite.

In some embodiments, nucleic acids of the invention are obtained from any mammalian parasite. In one embodiment, the parasite is a worm. In another embodiment, the parasite is a malaria-causing parasite. In another embodiment, the parasite is a Leishmaniasis-causing parasite. In another embodiment, the parasite is an amoeba.

In some embodiments the pathogen is a non-mammalian pathogen (is pathogenic in non-mammalian organisms).

In one embodiment, the nucleic acids of the invention include nucleic acids that are targets of gNAs and nucleic acids that are not the targets of gNAs, in the same sample.

In one embodiment, the nucleic acids of the invention include nucleic acids that are targets of gRNAs and nucleic acids that are not the targets of gRNAs, in the same sample.

In one embodiment, the nucleic acids of the invention include nucleic acids that are targets of gDNAs and nucleic acids that are not the targets of gDNAs, in the same sample.

In one embodiment, the nucleic acids of the invention include target nucleic acids (targets of gNAs) and nucleic acids of interest (not targeted by gNAs) from a sample.

In one embodiment, the nucleic acids of the invention include target nucleic acids (targets of gRNAs) and nucleic acids of interest (not targeted by gRNAs) from a sample.

In one embodiment, the nucleic acids of the invention include target nucleic acids (targets of gDNAs) and nucleic acids of interest (not targeted by gDNAs) from a sample.

In one embodiment, the target DNA (target of the gNAs, gRNAs, gDNAs) may be human non-mitochondrial DNA (e.g. genomic DNA), and the DNA of interest (for capture) may be the human mitochondrial DNA, and the human mitochondrial DNA is enriched by targeting the non-mitochondrial human DNA.

In one embodiment, the nucleic acids to be captured may be a non-mapable region of a genome; and the nucleic acids to be retained for further analysis/sequencing/cloning may be mapable regions of a genome. In one embodiment, the nucleic acids to be captured out may be a mapable region of a genome; and the nucleic acids to be retained for further analysis/sequencing/cloning may be non-mapable regions of a genome. Examples of non mapable regions include telomeres, centromeres, or other genomic regions that contain features harder to map.

In one embodiment, the nucleic acids of the invention are obtained from a biological sample. The biological sample from which the nucleic acids are obtained include but are not limited to whole blood, plasma, serum, tears, saliva, mucous, cerebrospinal fluid, teeth, bone, fingernails, feces, urine, tissue, and biopsy. The biological sample may include forensic samples such as teeth, bone, fingernails or the like. The biological sample may include tissue, a tissue biopsy, for example a resected lung tissue. The biological sample may include a clinical sample, which refers to a sample obtained in a clinical setting, such as in a hospital, or clinic.

In one embodiment, the nucleic acids of the invention are obtained from an environmental sample, for example from water, soil, air, or rock.

In one embodiment, the nucleic acids of the invention are obtained from a forensic sample, for example, a sample obtained from an individual at a crime scene, from a piece of evidence, post-mortem, as a part of an ongoing investigation or the like.

In on embodiment, the nucleic acids of the invention are provided in a library.

The nucleic acids of the invention can be either provided or extracted from a sample. Extraction can extract substantially all the nucleic acid sequences from a specimen.

The methods of the invention may produce nucleic acids to be captured: nucleic acids to not be captured at a ratio of anywhere between 99.999:0.001 to 0.001:99.999. The methods of the invention may produce targeted nucleic acids and nucleic acids of interest at a ratio of anywhere between 99.999:0.001 to 0.001:99.999. The methods of the invention may produce nucleic acids to be captured to nucleic acids to be retained/analyzed/sequenced at a ratio of anywhere between 99.999:0.001 to 0.001:99.999. In these embodiments, the ratios can be equal to or fall anywhere in between 99.999:0.001 to 0.001:99.999, for example the ratio can be 99:1, 95:5, 90:10, 85:15, 80:20, 75:25, 70: 30, 65:35, 60:40, 55:45, 50:50, 45:55, 40:60, 35:65, 30:70, 25:75, 20:80, 15:85, 10:90, 5:95, and 1:99.

After the capture, the captured or retained nucleic sequences can be fragmented to reduce the lengths of each extracted nucleic acids to a more manageable length for amplifying, sequencing or the like.

As provided herein, at least 10%, 15%, 20%, 25%, 30%, 40%, 50%, 60%, 70%, 80%, 90% of the starting nucleic acid material can be captured. This capture can be achieved in no greater than 10 minutes, 15 minutes, 20 minutes, 30 minutes, 45 minutes, 60 minutes, 75 minutes, 90 minutes, 105 minutes, 120 minutes, 150 minutes, 180 minutes, or 240 minutes.

In some cases, the targeted sites of interest represent less than 90%, less than 80%, less than 70%, less than 60%, less than 50%, less than 40%, less than 30%, less than 20%, or less than 10% of the total DNA in the sample.

Adapters

As provided herein, the nucleic acids of the invention (referred to interchangeably as nucleic acids or nucleic acid fragments) are adapter-ligated, to aid in carrying out the methods provided herein.

Nucleic acids of the invention to be adapter-ligated can range from 20 bp in size to 5000 bp in size. For example, the nucleic acid to be adapter-ligated may be at least 20, 25, 50, 75, 100, 125, 150, 175, 200, 25, 300, 350, 400, 450, 500, 550, 600, 650, 700, 750, 800, 850, 900, 950, 1000, 1500, 2000, 2500, 3000, 3500, 4000, 4500, or 5000 bp. In one specific embodiment, the nucleic acid to be adapter ligated is 100 bp. In one specific embodiment, the nucleic acid to be adapter ligated is 200 bp. In one specific embodiment, the nucleic acid to be adapter ligated is 300 bp. In one specific embodiment, the nucleic acid to be adapter ligated is 400 bp. In one specific embodiment, the nucleic acid to be adapter ligated is 500 bp.

An adapter can be ligated to each end of each of the nucleic acids, or nucleic acid fragments, at the 5' and 3' ends. In other embodiments an adapter may be ligated to only one end of each of the fragments or in other instances adapters may be ligated in a later step. In one example the adapter is a nucleic acid that is ligatable to both strands of a double-stranded DNA molecule. In various embodiments the adapter may be a hairpin adapter e.g., one molecule that base pairs with itself to form a structure that has a double-stranded stem and a loop, where the 3' and 5' ends of the molecule ligate to the 5' and 3' ends of the double-stranded DNA molecule of the fragment, respectively. Alternately, the adapter may be a Y-adapter ligated to one end or to both ends of a fragment, also called a universal adapter. Alternately, the adapter may itself be composed of two distinct oligonucleotide molecules that are base paired with one another. Additionally, a ligatable end of the adapter may be designed to be compatible with overhangs made by cleavage by a restriction enzyme, or it may have blunt ends or a 5' T overhang. Generally, the adapter may include double-stranded as well as single-stranded molecules. Thus the adapter can be DNA or RNA, or a mixture of the two. Adapters containing RNA may be cleavable by RNase treatment or by alkaline hydrolysis.

Adapters can be 10 to 100 bp in length although adapters outside of this range are usable without deviating from the present invention. In specific embodiments, the adapter is at least 10 bp, at least 15 bp, at least 20 bp, at least 25 bp, at least 30 bp, at least 35 bp, at least 40 bp, at least 45 bp, at least 50 bp, at least 55 bp, at least 60 bp, at least 65 bp, at least 70 bp, at least 75 bp, at least 80 bp, at least 85 bp, at least 90 bp, or at least 95 bp in length.

In further examples the captured nucleic acid sequences may be derived from one or more DNA sequencing libraries. An adapter may be configured for a next generation sequencing platform, for example for use on an Illumina sequencing platform or for use on an IonTorrent platform.

An adapter may contain a restriction site of interest or a primer binding site.

Exemplary adapters include P5 and P7 adapters.

Guide Nucleic Acids (gNAs)

Provided herein are guide nucleic acids (gNAs), wherein the gNAs are complementary to (selective for, can hybridize with) targeted sites or sequences of interest, or sequences not of interest in the nucleic acids, for example in genomic DNA from a host. The gNAs guide nucleic acid-guided nucleases to specific sites on a nucleic acid.

In some embodiments, the gNAs are guide RNAs (gRNAs); in other embodiments, the gNAs are guide DNAs (gDNAs). In some embodiments the gNAs comprise a mixture of gRNAs and gDNAs.

The host to which the gNAs are directed to can be an animal, for example a human, cow, horse, sheep, pig, monkey, dog, cat, gerbil, bird, mouse, or rat. The host can be a plant. The non-host can be a prokaryotic organism, a eukaryote, a virus, a bacterium, a fungus, and a protozoan.

In one embodiment, the present invention provides a guide nucleic acid (gNA) library which comprises a collection of gNAs, configured to hybridize with a nucleic acid sequence targeted for capture. In another embodiment, the present invention provides a guide NA library which comprises a collection of gNAs, configured to hybridize with a nucleic acid sequence that is not targeted for capture.

In one embodiment, the present invention provides a guide RNA library which comprises a collection of gRNAs, configured to hybridize with a nucleic acid sequence targeted for capture. In another embodiment, the present invention provides a guide RNA library which comprises a collection of gRNAs, configured to hybridize with a nucleic acid sequence that is not targeted for capture.

In one embodiment, the present invention provides a guide DNA library which comprises a collection of gDNAs, configured to hybridize with a nucleic acid sequence targeted for capture. In another embodiment, the present invention provides a guide DNA library which comprises a collection of gDNAs, configured to hybridize with a nucleic acid sequence that is not targeted for capture.

In one embodiment, the gNAs are selective for target nucleic acids in a sample, but are not selective for sequences of interest from the sample.

In one embodiment, the gNAs are used to serially capture nucleic acid sequences.

In some embodiments, the gNAs are selective for a target nucleic acid sequences which are followed by Protospacer Adjacent Motif (PAM) sequences that can be bound by a nucleic acid-guided nuclease. In some embodiments, the sequence of the gNAs is determined by the nucleic acid-guided nuclease type. In various embodiments the gNAs may be tailored to different nucleic acid-guided nuclease types as the PAM sequence can vary by the species of the organism from which the nucleic acid-guided nuclease is derived.

The gNAs (gRNAs or gDNAs) of the invention can range in size from 50-200 base pairs. For example, a gNA of the invention can be at least 50 bp, 55 bp, 60 bp, 65 bp, 70 bp, 75 bp, 80 bp, 85 bp, 90 bp, 95 bp, 100 bp, 110 bp, 120 bp, 125 bp, 130 bp, 140 bp, 150 bp, 160 bp, 170 bp, 175 bp, 180 bp, 190 bp, or 195 bp. In specific embodiments, the gNA is 80 bp, 90 bp, 100 bp, or 110 bp. In some embodiments, a target-specific gNA comprises a base pair sequence can be complementary to a pre-defined site in a target nucleic acid that is followed by a Protospacer Adjacent Motif or (PAM) sequence that can be bound by a nucleic acid-guided nuclease protein (e.g. Cas9) derived from a bacterial species. In specific embodiments, the base pair sequence of the gNA that is complementary to a pre-defined site in a target nucleic acid is 15, 16, 17, 18, 19, 20, 25, 30, 35, 40, 45, or 50 base pairs.

The present invention also provides for gNA libraries (e.g. gRNA libraries or gDNA libraries). A gNA library can comprise a number of different species-specific guide NA (e.g. gRNA or gDNA) elements each, configured to hybridize with (be selective for) a nucleic acid sequence being targeted capture, a nucleic acid sequence of interest, or a nucleic acid sequence not of interest. Each gNA includes a target-specific guide sequence and a stem loop binding site that is formed to bind with a nucleic acid-guided nuclease protein. In some embodiments, the library can comprise a plurality of different guide NAs, each having a different 15-30 base pair sequence that is complementary to a different pre-defined site in the nucleic acid being targeted, that is followed by an appropriate PAM sequence that can be bound by a nucleic acid-guided nuclease protein. For each guide NA the PAM sequence is present in the pre-defined DNA or RNA target sequence of the nucleic acid of interest but is not present in the corresponding target specific guide sequence.

Generally according to the present invention, any nucleic acid sequence in a genome of interest, with a pre-defined target sequence followed by the appropriate PAM sequence can be hybridized by a corresponding guide RNA provided in the guide NA library and bound by a nucleic acid-guided nuclease. In various embodiments the gNA library may be tailored to different nucleic acid-guided nuclease types since the PAM sequence can vary by the species of the bacteria from which nucleic acid-guided nuclease is derived. But in some variations, the pre-defined target sequence is not followed by a PAM sequence.

Different target-specific sequences in the gNAs can be generated. This can be done by using a promoter for a bacteriophage RNA polymerase, e.g., the RNA polymerase from bacteriophage T3, T7, SP6 or the like. Accordingly, each different T7 RNA polymerase promoter provides a different target specific sequence suitable for hybridizing to a different target nucleic acid sequence. A non-limiting exemplary set of forward primers usable for both annealing and subsequent PCR reactions is listed in Table 1 provided below.

A gNA library (e.g. a gRNA or gDNA library) can be amplified to include a large number of copies of each different guide NA element as well as a large number of different guide NA elements as may be suitable to for the desired capture results. The number of unique guide NA elements in a given guide NA library may range from 1 unique guide NA element to as many as 300,000,000 unique guide NA elements, or approximately 1 unique guide NA sequence for every 10 base pairs in the human genome. The number of unique gNAs (e.g., gRNAs or gDNAs) can be at least about $10^1, 10^2, 10^3, 10^4, 10^5, 10^6, 10^7,$ or $10^8$ unique gNAs. The number of unique gNAs can result in that number of unique nucleic acid-guided nuclease—gNA complexes (e.g. CRISPR/Cas system protein-gRNA complexes).

Without being limited to theory, the distance between gNAs to arrive at >95% cleavage of the target nucleic acid can be computed, if the gNAs display ~100% efficacy: this can be computed by measuring the distribution of library size and determining the mean, N and the standard deviation SD; N-2SD=minimum size for >95% of the library, ensuring that there is one guide NA per fragment of this size to ensure >95% capture. This can also be described as the Maximum distance between guide NAs=Mean of library size−2×(standard deviation of library size).

In various embodiments of the invention, the gNAs can be specific for various targeted sites of interest, including, but not limited to, single nucleotide polymorphisms (SNPs), short tandem repeats (STRs), cancer genes, inserts, deletions, structural variations, exons, genetic mutations, and regulatory regions.

Nucleic Acid-Guided Nucleases

Provided herein compositions and methods for the capture of nucleic acids from a sample. These compositions and methods utilize nucleic acid-guided nucleases. As used herein, a "nucleic acid-guided nuclease" is any endonuclease that cleaves DNA, RNA or DNA/RNA hybrids, and which uses one or more nucleic acid guide nucleic acids (gNAs) to confer specificity. Nucleic acid-guided nucleases include CRISPR/Cas system proteins as well as non-CRISPR/Cas system proteins.

The nucleic acid-guided nucleases provided herein can be DNA guided DNA endonucleases; DNA guided RNA endonucleases; RNA guided DNA endonucleases; or RNA guided RNA endonucleases.

In one embodiment, the nucleic acid-guided nuclease is a nucleic acid-guided-DNA endonuclease.

In one embodiment, the nucleic acid-guided nuclease is a nucleic acid-guided-RNA endonuclease.

CRISPR/Cas System Nucleic Acid-Guided Nucleases

In some embodiments, CRISPR/Cas system proteins are used in the embodiments provided herein. In some embodiments, CRISPR/Cas system proteins include proteins from CRISPR Type I systems, CRISPR Type II systems, and CRISPR Type III systems.

In some embodiments, CRISPR/Cas system proteins can be from any bacterial or archaeal species.

In some embodiments, the CRISPR/Cas system protein is isolated, recombinantly produced, or synthetic.

In some embodiments, the CRIPR/Cas system proteins are from, or are derived from CRISPR/Cas system proteins from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis,* or *Corynebacter diphtheria.*

In some embodiments, examples of CRISPR/Cas system proteins can be naturally occurring or engineered versions.

In some embodiments, naturally occurring CRISPR/Cas system proteins can belong to CAS Class I Type I, III, or IV, or CAS Class II Type II or V, and can include Cas9, Cas3, Cas8a-c, Cas10, Cse1, Csy1, Csn2, Cas4, Csm2, Cmr5, Csf1, C2c2, and Cpf1.

In an exemplary embodiment, the CRISPR/Cas system protein comprises Cas9.

A "CRISPR/Cas system protein-gNA complex" refers to a complex comprising a CRISPR/Cas system protein and a guide NA (e.g. a gRNA or a gDNA). Where the gNA is a gRNA, the gRNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences.

A CRISPR/Cas system protein may be at least 60% identical (e.g., at least 70%, at least 80%, or 90% identical, at least 95% identical or at least 98% identical or at least 99% identical) to a wild type CRISPR/Cas system protein. The CRISPR/Cas system protein may have all the functions of a wild type CRISPR/Cas system protein, or only one or some of the functions, including binding activity, nuclease activity, and nuclease activity.

The term "CRISPR/Cas system protein-associated guide NA" refers to a guide NA. The CRISPR/Cas system protein-associated guide NA may exist as isolated NA, or as part of a CRISPR/Cas system protein-gNA complex.

Cas9

In some embodiments the CRISPR/Cas System protein nucleic acid-guided nuclease is or comprises Cas9. The Cas9 of the present invention can be isolated, recombinantly produced, or synthetic.

Examples of Cas9 proteins that can be used in the embodiments herein can be found in F. A. Ran, L. Cong, W. X. Yan, D. A. Scott, J. S. Gootenberg, A. J. Kriz, B. Zetsche, O. Shalem, X. Wu, K. S. Makarova, E. V. Koonin, P. A. Sharp, and F. Zhang; "In vivo genome editing using *Staphylococcus aureus* Cas9," Nature 520, 186-191 (9 Apr. 2015) doi:10.1038/nature14299, which is incorporated herein by reference.

In some embodiments, the Cas9 is a Type II CRISPR system derived from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis,* or *Corynebacter diphtheria*.

In some embodiments, the Cas9 is a Type II CRISPR system derived from *S. pyogenes* and the PAM sequence is NGG located on the immediate 3' end of the target specific guide sequence. The PAM sequences of Type II CRISPR systems from exemplary bacterial species can also include: *Streptococcus pyogenes* (NGG), *Staph aureus* (NNGRRT), *Neisseria meningitidis* (NNNNGA TT), *Streptococcus thermophilus* (NNAGAA) and *Treponema denticola* (NAAAAC) which are all usable without deviating from the present invention.

In one exemplary embodiment, Cas9 sequence can be obtained, for example, from the pX330 plasmid (available from Addgene), re-amplified by PCR then cloned into pET30 (from EMD biosciences) to express in bacteria and purify the recombinant 6His tagged protein.

A "Cas9-gNA complex" refers to a complex comprising a Cas9 protein and a guide NA. A Cas9 protein may be at least 60% identical (e.g., at least 70%, at least 80%, or 90% identical, at least 95% identical or at least 98% identical or at least 99% identical) to a wild type Cas9 protein, e.g., the *Streptococcus pyogenes* Cas9 protein. The Cas9 protein may have all the functions of a wild type Cas9 protein, or only one or some of the functions, including binding activity, nuclease activity, and nuclease activity.

The term "Cas9-associated guide NA" refers to a guide NA as described above. The Cas9-associated guide NA may exist isolated, or as part of a Cas9-gNA complex.

Non-CRISPR/Cas System Nucleic Acid-Guided Nucleases

In some embodiments, non-CRISPR/Cas system proteins are used in the embodiments provided herein.

In some embodiments, the non-CRISPR/Cas system proteins can be from any bacterial or archaeal species.

In some embodiments, the non-CRISPR/Cas system protein is isolated, recombinantly produced, or synthetic.

In some embodiments, the non-CRISPR/Cas system proteins are from, or are derived from *Aquifex aeolicus, Thermus thermophilus, Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis, Natronobacterium gregoryi,* or *Corynebacter diphtheria*.

In some embodiments, the non-CRISPR/Cas system proteins can be naturally occurring or engineered versions.

In some embodiments, a naturally occurring non-CRISPR/Cas system protein is NgAgo (Argonaute from *Natronobacterium gregoryi*).

A "non-CRISPR/Cas system protein-gNA complex" refers to a complex comprising a non-CRISPR/Cas system protein and a guide NA (e.g. a gRNA or a gDNA). Where the gNA is a gRNA, the gRNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences.

A non-CRISPR/Cas system protein may be at least 60% identical (e.g., at least 70%, at least 80%, or 90% identical, at least 95% identical or at least 98% identical or at least 99% identical) to a wild type non-CRISPR/Cas system protein. The non-CRISPR/Cas system protein may have all the functions of a wild type non-CRISPR/Cas system protein, or only one or some of the functions, including binding activity, nuclease activity, and nuclease activity.

The term "non-CRISPR/Cas system protein-associated guide NA" refers to a guide NA. The non-CRISPR/Cas system protein-associated guide NA may exist as isolated NA, or as part of a non-CRISPR/Cas system protein-gNA complex.

Catalytically Dead Nucleic Acid-Guided Nucleases

In some embodiments, engineered examples of nucleic acid-guided nucleases include catalytically dead nucleic acid-guided nucleases (CRISPR/Cas system nucleic acid-guided nucleases or non-CRISPR/Cas system nucleic acid-guided nucleases). The term "catalytically dead" generally refers to a nucleic acid-guided nuclease that has inactivated nucleases, for example inactivated HNH and RuvC nucleases. Such a protein can bind to a target site in any nucleic acid (where the target site is determined by the guide NA), but the protein is unable to cleave or nick the nucleic acid.

Accordingly, the catalytically dead nucleic acid-guided nuclease allows separation of the mixture into unbound nucleic acids and catalytically dead nucleic acid-guided nuclease-bound fragments. Use of a dead nucleic acid-guided nuclease is depicted, for example, in FIG. 9 and FIG. 10, in Protocols 3 And 4, respectively. In one exemplary embodiment, a dCas9/gRNA complex binds to the targets determined by the gRNA sequence. The dCas9 bound can prevent cutting by Cas9 while other manipulations proceed, as pictured in FIG. 10.

In another embodiment, the catalytically dead nucleic acid-guided nuclease can be fused to another enzyme, such as a transposase, to target that enzyme's activity to a specific site.

In some embodiments, the catalytically dead nucleic acid-guided nuclease is dCas9, dCpf1, dCas3, dCas8a-c, dCas10, dCse1, dCsy1, dCsn2, dCas4, dCsm2, dCm5, dCsf1, dC2C2, or dNgAgo.

In one exemplary embodiment the catalytically dead nucleic acid-guided nuclease protein is a dCas9.

Nucleic Acid-Guided Nuclease Nickases

In some embodiments, engineered examples of nucleic acid-guided nucleases include nucleic acid-guided nuclease nickases (referred to interchangeably as nickase nucleic acid-guided nucleases).

In some embodiments, engineered examples of nucleic acid-guided nucleases include CRISPR/Cas system nickases or non-CRISPR/Cas system nickases, containing a single inactive catalytic domain.

In some embodiments, the nucleic acid-guided nuclease nickase is a Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, or a NgAgo nickase.

In one embodiment, the nucleic acid-guided nuclease nickase is a Cas9 nickase.

In some embodiments, a nucleic acid-guided nuclease nickase can be used to bind to target sequence. With only one active nuclease domain, the nucleic acid-guided nuclease nickase cuts only one strand of a target DNA, creating a single-strand break or "nick". Depending on which mutant is used, the guide NA-hybridized strand or the non-hybridized strand may be cleaved. nucleic acid-guided nuclease nickases bound to 2 gNAs that target opposite strands can create a double-strand break in the nucleic acid. This "dual nickase" strategy increases the specificity of cutting because it requires that both nucleic acid-guided nuclease/gNA complexes be specifically bound at a site before a double-strand break is formed.

In exemplary embodiments, a Cas9 nickase can be used to bind to target sequence. The term "Cas9 nickase" refers to a modified version of the Cas9 protein, containing a single inactive catalytic domain, i.e., either the RuvC- or the HNH-domain. With only one active nuclease domain, the Cas9 nickase cuts only one strand of the target DNA, creating a single-strand break or "nick". Depending on which mutant is used, the guide RNA-hybridized strand or the non-hybridized strand may be cleaved. Cas9 nickases bound to 2 gRNAs that target opposite strands will create a double-strand break in the DNA. This "dual nickase" strategy can increase the specificity of cutting because it requires that both Cas9/gRNA complexes be specifically bound at a site before a double-strand break is formed.

Capture of DNA can be carried out using a nucleic acid-guided nuclease nickase. This is illustrated in FIG. 6 and FIG. 11, Protocols 2 and 5, respectively. In one exemplary embodiment, as pictured in FIGS. 6 and 11, a nucleic acid-guided nuclease nickase cuts a single strand of double stranded nucleic acid, wherein the double stranded region comprises methylated nucleotides.

Dissociable and Thermostable Nucleic Acid-Guided Nucleases

In some embodiments thermostable nucleic acid-guided nucleases are used in the methods provided herein (thermostable CRISPR/Cas system nucleic acid-guided nucleases or thermostable non-CRISPR/Cas system nucleic acid-guided nucleases). In such embodiments, the reaction temperature is elevated, inducing dissociation of the protein; the reaction temperature is lowered, allowing for the generation of additional cleaved target sequences. In some embodiments, thermostable nucleic acid-guided nucleases maintain at least 50% activity, at least 55% activity, at least 60% activity, at least 65% activity, at least 70% activity, at least 75% activity, at least 80% activity, at least 85% activity, at least 90% activity, at least 95% activity, at least 96% activity, at least 97% activity, at least 98% activity, at least 99% activity, or 100% activity, when maintained for at least 75° C. for at least 1 minute. In some embodiments, thermostable nucleic acid-guided nucleases maintain at least 50% activity, when maintained for at least 1 minute at least at 75° C., at least at 80° C., at least at 85° C., at least at 90° C., at least at 91° C., at least at 92° C., at least at 93° C., at least at 94° C., at least at 95° C., 96° C., at least at 97° C., at least at 98° C., at least at 99° C., or at least at 100° C. In some embodiments, thermostable nucleic acid-guided nucleases maintain at least 50% activity, when maintained at least at 75° C. for at least 1 minute, 2 minutes, 3 minutes, 4 minutes, or 5 minutes. In some embodiments, a thermostable nucleic acid-guided nucleases maintains at least 50% activity when the temperature is elevated, lowered to 25° C.-50° C. In some embodiments, the temperature is lowered to 25° C., to 30° C., to 35° C., to 40° C., to 45° C., or to 50° C. In one exemplary embodiment, a thermostable enzyme retains at least 90% activity after 1 min at 95° C.

In some embodiments, the thermostable nucleic acid-guided nuclease is thermostable Cas9, thermostable Cpf1, thermostable Cas3, thermostable Cas8a-c, thermostable Cas10, thermostable Cse1, thermostable Csy1, thermostable Csn2, thermostable Cas4, thermostable Csm2, thermostable Cm5, thermostable Csf1, thermostable C2C2, or thermostable NgAgo.

In some embodiments the thermostable CRISPR/Cas system protein is thermostable Cas9.

Thermostable nucleic acid-guided nucleases can be isolated, for example, identified by sequence homology in the genome of thermophilic bacteria *Streptococcus thermophilus* and *Pyrococcus furiosus*. Nucleic acid-guided nuclease genes can then be cloned into an expression vector. In one exemplary embodiment, a thermostable Cas9 protein is isolated.

In another embodiment, a thermostable nucleic acid-guided nuclease can be obtained by in vitro evolution of a non-thermostable nucleic acid-guided nuclease. The sequence of a nucleic acid-guided nuclease can be mutagenized to improve its thermostability.

Exemplary Compositions of the Invention

In one embodiment, provided herein is a composition comprising a nucleic acid fragment, a nickase nucleic acid-guided nuclease-gNA complex, and labeled nucleotides. In one exemplary embodiment, provided herein is a composition comprising a nucleic acid fragment, a nickase Cas9-gRNA complex, and labeled nucleotides. In such embodiments, the nucleic acid may comprise DNA. The nucleotides can be labeled, for example with biotin. The nucleotides can be part of an antibody-conjugate pair.

In one embodiment, provided herein is a composition comprising a nucleic acid fragment and a catalytically dead nucleic acid-guided nuclease-gNA complex, wherein the catalytically dead nucleic acid-guided nuclease is fused to a transposase. In one exemplary embodiment, provided herein is a composition comprising a DNA fragment and a dCas9-gRNA complex, wherein the dCas9 is fused to a transposase.

In one embodiment, provided herein is a composition comprising a nucleic acid fragment comprising methylated nucleotides, a nickase nucleic acid-guided nuclease-gNA complex, and unmethylated nucleotides. In an exemplary embodiment, provided herein is a composition comprising a DNA fragment comprising methylated nucleotides, a nickase Cas9-gRNA complex, and unmethylated nucleotides.

In one embodiment, provided herein is a gDNA complexed with a nucleic acid-guided-DNA endonuclease. In an exemplary embodiment, the nucleic acid-guided-DNA endonuclease is NgAgo.

In one embodiment, provided herein is a gDNA complexed with a nucleic acid-guided-RNA endonuclease.

In one embodiment, provided herein is a gRNA complexed with a nucleic acid-guided-DNA endonuclease.

In one embodiment, provided herein is a gRNA complexed with a nucleic acid-guided-RNA endonuclease. In one embodiment the nucleic acid-guided-RNA endonuclease comprises C2c2.

Kits and Articles of Manufacture

The present application provides kits comprising any one or more of the compositions described herein, including, but not limited to, adapters, gNAs, gDNAs, gRNAs, gNA libraries, gRNA libraries, gDNA libraries, a nucleic acid-guided nuclease, a catalytically deade nucleic acid-guided nuclease, a nickase nucleic acid-guided nuclease, a CRISPR/Cas system protein, a nickase CRISPR/Cas system protein, a catalytically dead CRISPR/Cas system protein, Cas9, dCas9, Cas9 nickase, methylated nucleotides, labeled nucleotides, biotinylated nucleotides, avidin, streptavidin, an enzyme capable of initiating nucleic acid synthesis at a nicked site, DNA Polymerase I, TAQ polymerase, bst DNA Polymerase, an enzyme capable of cleaving methylated nucleotides, a DpnI enzyme, and an enzyme capable of methylating DNA, for example a Dam/Dcm1 methyltransferase).

In one embodiment, the kit comprises a collection or library of gNAs wherein the gNAs are targeted to human genomic DNA sequences, for example particular genes of interest (e.g. cancer genes) SNPs, STRs. In another exemplary embodiment, the kit comprises a collection or library of gNAs wherein the gNAs are targeted to non-human mammalian DNA sequences. In another exemplary embodiment, the kit comprises a collection or library of gNAs wherein the gNAs are targeted to human ribosomal RNA sequences. In another exemplary embodiment, the kit comprises a collection or library of gNAs wherein the gNAs are targeted to human mitochondrial DNA sequences.

In one exemplary embodiment, the kit comprises a collection or library of gRNAs wherein the gRNAs are targeted to human genomic DNA sequences, for example particular genes of interest (e.g. cancer genes) SNPs, STRs. In another exemplary embodiment, the kit comprises a collection or library of gRNAs wherein the gRNAs are targeted to non-human mammalian DNA sequences. In another exemplary embodiment, the kit comprises a collection or library of gRNAs wherein the gRNAs are targeted to human ribosomal RNA sequences. In another exemplary embodiment, the kit comprises a collection or library of gRNAs wherein the gRNAs are targeted to human mitochondrial DNA sequences.

The present application also provides articles of manufacture comprising any one of the kits described herein. Examples of an article of manufacture include vials (including sealed vials).

The following examples are included for illustrative purposes and are not intend to limit the scope of the invention.

EXAMPLES

Example 1: Capture of Mitochondrial DNA from Total Human Genomic DNA (Protocol 1 for Capture of DNA)

Overview

The objective of this method was to capture mitochondrial DNA from a library of human genomic DNA, as depicted in FIG. 1. A human tissue specimen was subjected to DNA extraction protocols, resulting in a DNA sample comprising >99% human DNA and <1% target sequence. The DNA sample was subjected to sequencing library construction protocols, resulting in a nucleic acid library comprising sequencing indexed adapters. To produce a library of target-specific guide RNAs (gRNAs), a library of target specific gRNA precursors, each comprising a T7 RNA polymerase promoter, a human-specific 20-base pair region, and a stem-loop binding site for Cas9, was subjected to in vitro transcription, yielding a library of target-specific guide RNAs. The library of target-specific guide RNAs was then combined with Cas9 proteins to yield a library of Cas9-gRNA complexes. The Cas9-gRNA complexes were then combined with the nucleic acid library such that the Cas9 cleaved matching target DNA sequences and left other DNA uncleaved. Second adapters were added and allowed to ligate specifically to the 5' phosphorylated blunt ends of cleaved DNA. PCR was then used to amplify specifically using the first and second adapters.

Mitochondrial DNA makes up approximately 0.1-0.2% of total human genomic DNA. To test the precise site-specific cutting of DNA with Cas9, followed by ligation of adapters, referring to FIG. 2, a test DNA (e.g., a plasmid) 201 was cut with Cas9 at a first location 202 or a second location 203, yielding either first products 204 or second products 205 (see, e.g., FIG. 2). Adapters were ligated 206 into the newly available blunt DNA ends. PCR amplification was performed for AUK-F/P7 or MB1OriR/P7, yielding two separate products per reaction. If the first location was cut, the products were 212 and 1.9 k in size; if the second location was cut, the products were 359 and 1.75 k in size. Verification was performed by sequencing.

Figure 4:
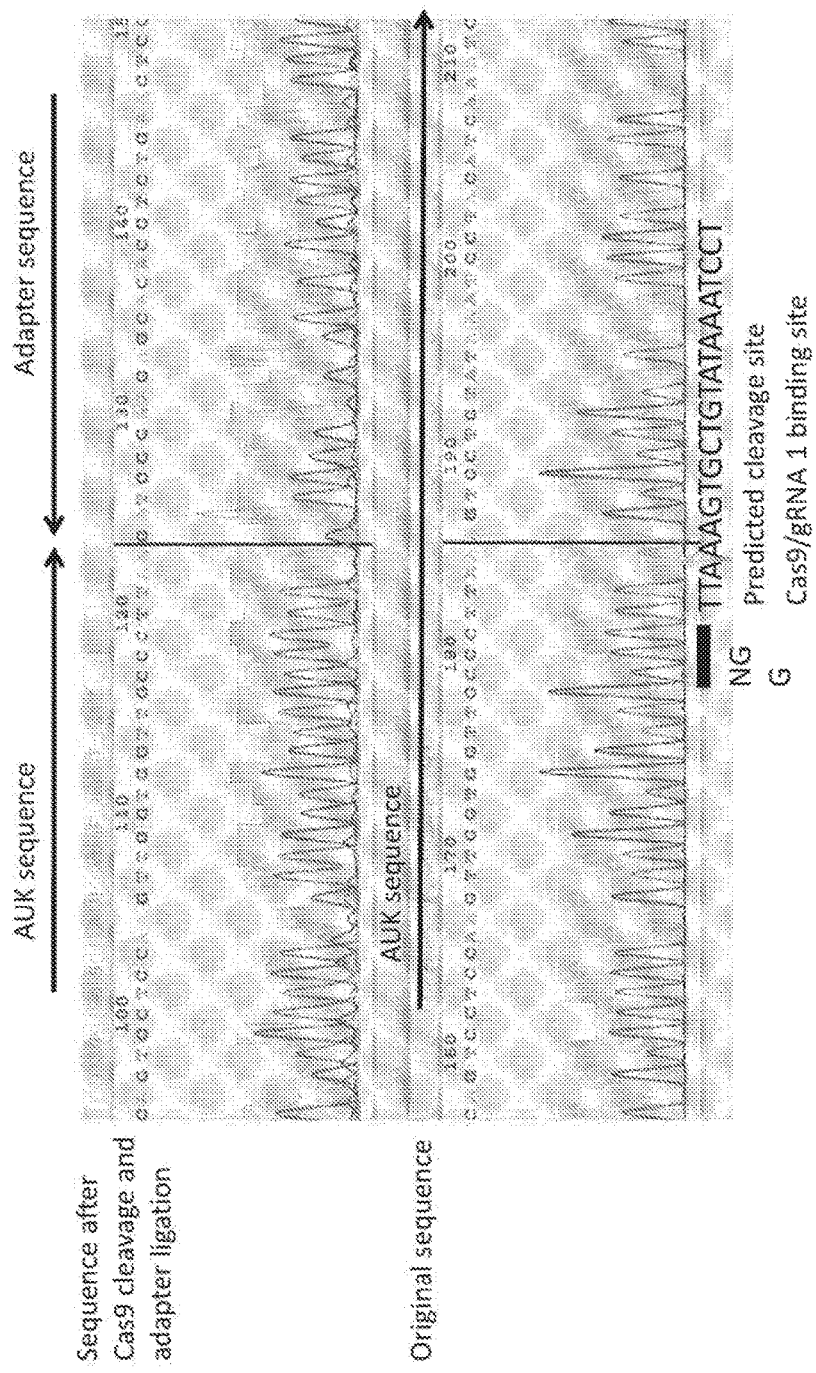
FIG. 4 illustrates that upon sequencing the amplified DNA, ligation of adapters occurred only at the location specified by the guide RNA. AUK sequence, after Cas9 cleavage and adapter ligation (upper left panel): SEQ ID NO: 1. Adapter sequence, after Cas9 cleavage and adapter ligation (upper right panel): SEQ ID NO: 2. AUK sequence, original sequence (lower panel: SEQ ID NO: 3. Cas9/gRNA1 binding site (at bottom): SEQ ID NO: 4.
Figure 5:
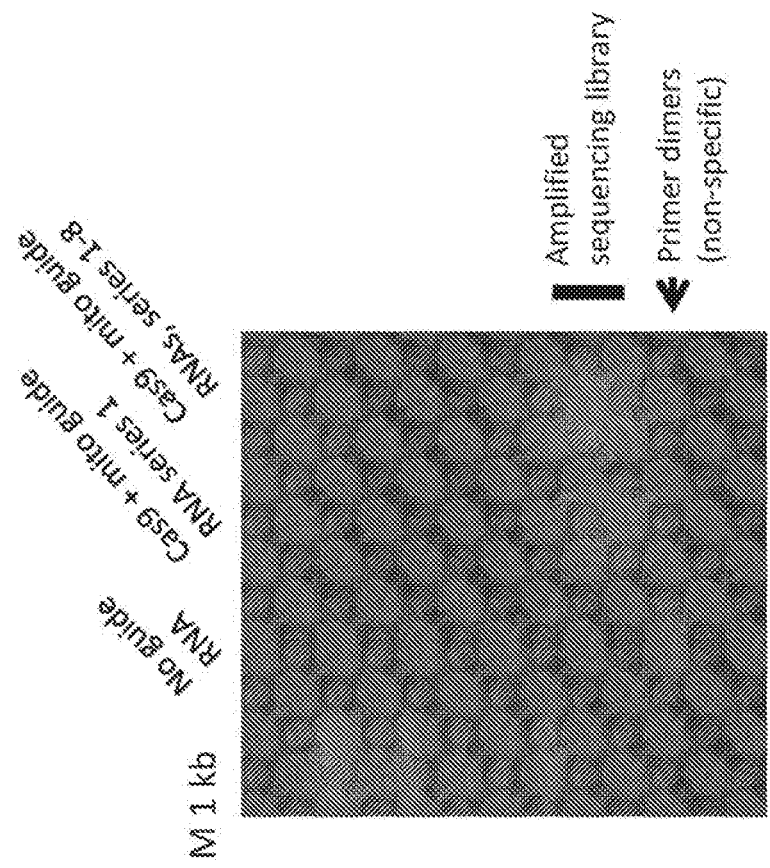
FIG. 5 illustrates that the method of FIG. 1 efficiently amplifies DNA that is under-represented in any given library.

Results showed that Cas9 cutting followed by ligation of adapters allowed for specific amplification of target DNA (see, e.g., FIG. 3); sequencing of the amplified DNA showed that ligation of adapters occurred only at the location specified by the guide RNA (see, e.g., FIG. 4).

Mitochondrial DNA was then enriched from a mixture containing predominantly human nuclear DNA. 25 guide RNAs specific for mitochondrial DNA were used, then cut with Cas9 and ligated with adapters, followed by amplification. As seen from FIG. 5, two separate reactions allowed for amplification of mitochondrial DNA whereas a reaction without guide RNAs did not amplify any DNA, thus showing that the method efficiently amplifies DNA that is under-represented in any given library.

Preparation of DNA Libraries

Human genomic DNA libraries were generated by end repairing 500 ng of fragmented human genomic DNA (ds DNA fragmentase, NEB, treated for 1 hour at 37° C.) using the blunt end repair kit (NEB) for 20 minutes at 25° C. Reactions were then heat inactivated at 75° C. for 20 minutes, cooled to 25° C. then ligated to 15 pmoles of P5/Myc adapters for two hours at 25° C. using T4 DNA ligase (NEB). Adapter dimmers were removed using the NGS cleanup kit (Life Technologies).

Expression of Cas9

Cas9 (from *S. pyogenes*) was cloned into the pET30 expression vector (EMD biosciences) to insert the hexahistidine tag immediately upstream of the Cas9 start codon. The resulting plasmid was transformed into the Rosetta (DE3) BL21 bacterial strain (EMD biosciences) and grown in 1 L of LB media with vigorous aeration until optical density of the culture (OD at 600 nm) reached 0.4. The temperature was lowered to 25° C., 0.2 mM IPTG was added and the culture grown for another four hours. Cells were then harvested by centrifugation (1,000×g for 20 min at 4° C.), resuspended in 10 ml binding buffer (20 mM Tris pH8, 0.5 M NaCl, 5 mM Imidazole, 0.05% NP40) and lysed by sonication (7×10 second bursts at 30% power, Sonifier 250, Branson). Insoluble cell debris were removed by centrifugation at 10,000×g for 20 min; supernatant containing soluble protein was then mixed with 0.4 ml of NTA beads (Qiagen) and loaded onto a column. Beads were washed three times with 4 ml binding buffer, then eluted with 3×0.5 ml of binding buffer supplemented with 250 mM Imidazole. Eluted fractions were then concentrated and buffer exchanged with storage buffer (10 mM Tris pH8, 0.3 M NaCl, 0.1 mM EDTA, 1 mM DTT, 50% glycerol) using a 30,000 MWCO protein concentrator (Life Technologies), verified by SDS PAGE followed by Colloidal Blue staining (Life Technologies), quantified, then stored at −20° C. for later use.

A mutant Cas9 nickase, a D10A mutant of S. pyogenes Cas9, can be produced and purified using the same procedures used to produce Cas9 as above.

Preparation of gRNA1 and gRNA2

Three oligonucleotides T7-guideRNA1 and 2 (sequences, in 5' to 3' direction GCCTCGAGCTAATACGACTCAC-TATAGGGATTTATACAGCACTTTAA (SEQ ID NO: 5), and GCCTCGAGCTAATACGACTCACTATAGGG- TCT-TTTTGGTCCTCGAAG (SEQ ID NO: 6)) and stlgR (sequence, GT TTT AGA GCT AGA AAT AGC AAG TTA AAA TAA GGC TAG TCC GTT ATC AAC TTG AAA AAG TGG CAC CGA GTC GGT GCT TTT TTT GGA TCC GAT GC (SEQ ID NO: 7)) were ordered and synthesized (IDT). The stlgR oligonucleotide (300 pmol) was sequentially 5' phosphorylated using T4 PNK (New England Biolabs) and then 5' adenylated sing the 5'adenylation kit (New England Biolabs), according to the manufacturer's instructions. T7-guide RNAs oligonucleotides (5 pmol) and the 5'adenylated stlgR (10 pmol) were then ligated using thermostable 5'App DNA/RNA ligase (New England Biolabs) at 65 C for one hour. Ligation reactions were heat inactivated at 90° C. for 5 min, then amplified by PCR (using OneTaq, New England Biolabs, 30 cycles of 95° C. 30 secs, 57° C. 20 secs, 72° C., 20 secs) with primers ForT7 (sequence GCC TCG AGC TAA TAC GAC TCA C (SEQ ID NO: 8)) and gRU (sequence AAAAAAAGCACCGACTCGGTG (SEQ ID NO: 9)). PCR products were purified using PCR cleanup kit (Life Technologies) and verified by agarose gel electrophoresis and sequencing. Verified products were then used as templates for in vitro transcription.

Preparation of Guide RNA Libraries

T7-guideRNA oligonucleotides (Table 1) and a separate oligonucleotide, stlgR (sequence, GT TTT AGA GCT AGA AAT AGC AAG TTA AAA TAA GGC TAG TCC GTT ATC AAC TTG AAA AAG TGG CAC CGA GTC GGT GCT TTT TTT GGA TCC GAT GC (SEQ ID NO: 7)) were ordered and synthesized (IDT).

The stlgR oligonucleotide (300 pmol) was sequentially 5' phosphorylated using T4 PNK (New England Biolabs) and then 5' adenylated sing the 5'adenylation kit (New England Biolabs), according to the manufacturer's instructions. T7-guide RNAs oligonucleotides (5 pmol) and the 5'adenylated stlgR (10 pmol) were then ligated using thermostable 5'App DNA/RNA ligase (New England Biolabs) at 65 C for one hour. Ligation reactions were heat inactivated at 90° C. for 5 min, then amplified by PCR (using OneTaq, New England Biolabs, 30 cycles of 95° C. 30 secs, 57° C. 20 secs, 72° C., 20 secs) with primers ForT7 (sequence GCC TCG AGC TAA TAC GAC TCA C (SEQ ID NO: 8)) and gRU (sequence AAAAAAAGCACCGACTCGGTG (SEQ ID NO: 9)). PCR products were purified using PCR cleanup kit (Life Technologies) and verified by agarose gel electrophoresis and sequencing. Verified products were then used as templates for in vitro transcription.

TABLE 1

Mito/T7 primers for ligation reactions

Series 1

| Name | Sequence |
|---|---|
| T7-1-F (SEQ ID NO: 10) | GCC TCG AGC TAA TAC GAC TCA CTA TAG GCT TGG ATT AGC GTT TAG AA |
| T7-13-F (SEQ ID NO: 11) | GCC TCG AGC TAA TAC GAC TCA CTA TAG GCT CTT AAA ACT AGG CGG CTA |
| T7-39-F (SEQ ID NO: 12) | GCC TCG AGC TAA TAC GAC TCA CTA TAG ATT TAC ACT CAC AAC ACC CT |
| T7-41-F (SEQ ID NO: 13) | GCC TCG AGC TAA TAC GAC TCA CTA TAG AAC AGC TAT CCA TTG GTC TT |
| T7-43-F (SEQ ID NO: 14) | GCC TCG AGC TAA TAC GAC TCA CTA TAG GCA GCC GGA AGC CTA TTC GC |
| T7-61-F (SEQ ID NO: 15) | GCC TCG AGC TAA TAC GAC TCA CTA TAG GTA ATG AGG ATG TAA GCC CG |
| T7-63-F (SEQ ID NO: 16) | GCC TCG AGC TAA TAC GAC TCA CTA TAG ATA TTT ACA AGA GGA AAA CC |
| T7-65-F (SEQ ID NO: 17) | GCC TCG AGC TAA TAC GAC TCA CTA TAG GTT TGA AGC TTA GGG AGA GCT |
| T7-67-F (SEQ ID NO: 18) | GCC TCG AGC TAA TAC GAC TCA CTA TAG GTA TGG CTT TGA AGA AGG CG |

Series 2

| Name | Sequence |
|---|---|
| T7mtgRNA3 (SEQ ID NO: 19) | GCC TCG AGC TAA TAC GAC TCA CTA TAG TAG ATG ACG GGT TGG GCC AG |
| T7mtgRNA7 (SEQ ID NO: 20) | GCC TCG AGC TAA TAC GAC TCA CTA TAG AGC TTT ACA GTG GGC TCT AG |
| T7mtgRNA11 (SEQ ID NO: 21) | GCC TCG AGC TAA TAC GAC TCA CTA TAG ATG GCA GCT TCT GTG GAA CG |
| T7mtgRNA15 (SEQ ID NO: 22) | GCC TCG AGC TAA TAC GAC TCA CTA TAG GTG GTA AGG GCG ATG AGT GT |
| T7mtgRNA31 (SEQ ID NO: 23) | GCC TCG AGC TAA TAC GAC TCA CTA TAG TCC ATA ACG CTC CTC ATA CT |
| T7mtgRNA33 (SEQ ID NO: 24) | GCC TCG AGC TAA TAC GAC TCA CTA TAG TCT CCC TTC ACC ATT TCC CA |

In Vitro Transcription

Verified products were then used as templates for in vitro transcription reactions using the HiScribe T7 transcription kit (New England Biolabs). 500-1000 ng of template was incubated overnight at 37° C. according to the manufacturer's instruction. To transcribe the guide libraries into guide RNA, we assembled the following in vitro transcription reaction mixture: 10 µl purified library (~500 ng), 6.5 µl of H2O, of 2.25 µl of ATP, 2.25 µl of CTP, 2.25 µl of GTP, 2.25 µl of UTP, 2.25 µl 10× reaction buffer (NEB) and 2.25 µl of T7 RNA polymerase mix. The reaction was incubated at 37° C. for 24 hours, then purified using the RNA cleanup kit (Life Technologies), eluted into 100 µl of RNase-free water, quantified and stored at −20° C. until use.

DNA-Specific Cas9-Mediated Fragmentation

For cutting the test DNA test guide RNA 1 and 2 were used separately. For cutting and enriching the mitochondrial DNA from a human genomic DNA library, guide RNA series 1 and 2 were used. Diluted guide RNA (1 ul, equivalent to 2 pmol) was combined with 3 ul 10× Cas9 reaction buffer (NEB), 20 ul H2O and 1 ul of recombinant Cas9 enzyme (NEB, 1 pmol/ul). A control reaction using a control guide RNA targeting the following sequence (5'-GGATTTATA-CAGCACTTTAA-3'(SEQ ID NO: 25)) was performed separately, using the same parameters. This sequence is absent from either the human chromosomal or mitochondrial DNA. Reactions were incubated for 15 min at 37° C., then supplemented with 5 µl diluted DNA library (50 pg/µl) and incubation at 37° C. continued for 90 min. The reactions were terminated by adding RNase A (Thermo Fisher Scientific) at a 1:100 dilution, then purifying the DNA using a PCR cleanup kit (LifeTechnologies) and eluting in 30 ul 10 mM Tris-Cl pH 8. Reactions were then stored at −20° C. until use.

Ligation of Adapters and PCR Analysis

For the test DNA, reactions after Cas9 digestion were incubated with 15 pmoles of P5/P7 adapters and T4 DNA ligase (NEB) for one hour at 25° C. Ligations were then used as templates for PCR using the TestDNA-F primer (sequence ATGCCGCAGCACTTGG (SEQ ID NO: 26)) and P5 primer (sequence AATGATACGGCGACCACCGA (SEQ ID NO: 27)). Successful PCR products were confirmed by agarose gel electrophoresis sequenced using the TestDNA-F primer (ElimBio), to show cutting and ligation occurred at the target DNA sequence.

Elimination of Adapters Ligated at Old Ends

For the enrichment of mitochondrial DNA, after Cas9 digestion, reactions were incubated with 15 pmoles of Flag5/P7 adapters and T4 DNA ligase (NEB) for one hour at 25° C. Multiple molecular biology methods can be employed to eliminate ligation of adapters at the ends of the old P5 and P7 adapters from the original library, for example with enzyme treatment. Reactions were then used as templates for PCR using the P7 (sequence CAAGCA-GAAGACGGCATACGA (SEQ ID NO: 28)) and P5 primers (sequence AATGATACGGCGACCACCGA (SEQ ID NO: 27)). Successful PCR products were confirmed by agarose gel electrophoresis.

Example 2: Using Cas9 Nickase to Label, then Purify Test DNA from a DNA Mixture (Protocol 2 for Capture of DNA)

Overview

The purpose of this method was to capture a region of interest (e.g., SNP, STR, etc.) from a library of human genomic DNA, as depicted for example in FIG. 6. To apply this protocol, a test DNA containing a site for a nicking enzyme guided by target-specific guide RNAs (NtAlwI (NEB)) was mixed at 1% or 5% into another pool of DNA that does not contain this site. Nickase Cas9 cleaves only at target sequence and only cuts one strand of DNA. Nickase was used to nick target sequences. Single strand cuts (nicks) are a substrate for DNA polymerase I which can be used to replace the DNA downstream of the nick with biotin labeled DNA. Biotinylated DNA of interest was then purified, amplified, and sequenced.

The mixture of DNA with 701 and without 702 target sites for nicking (e.g., GGATC) 703 was nicked 704 using NtAlwI (see, e.g., FIG. 7). DNA that does not have nickase sites was present in 100× excess compared to DNA of interest with the nickase sites. Single strand cuts (nicks) are a substrate for DNA polymerase I which are used to replace 705 the DNA downstream of the nick with biotin labeled DNA. Biotin-labeled DNA of interest was isolated by streptavidin binding and washing 706. PCR amplification was performed with specific primers 707, yielding amplified regions of interest 708 and amplified unlabeled sequences 709 present, for example, due to non-specific labeling or capture.

Two specific PCR reactions (one for the test DNA with regions of interest, the other for other DNA without regions of interest) showed that the test DNA had been enriched approximately 50-fold (see, e.g., FIG. 8).

Expression and Purification of Cas9 Nickase

A mutant Cas9 nickase, a D10A mutant of *S. pyogenes* Cas9, can be produced and purified using the same procedures used to produce Cas9 as above.

Sequence Specific Cas9 Nickase-Mediated Nicking

Diluted guide RNA, targeting the following sequence 5'-GGATTTATACAGCACTTTAA-3' (SEQ ID NO: 29) (1 ul, equivalent to 2 pmol) was combined with 3 ul 10× Cas9 reaction buffer (NEB), 20 ul H2O and 1 ul of recombinant Cas9 Nickase enzyme (10 pmol/ul). This target sequence is only present on the target DNA (that makes either 5% or 1% of the total DNA). Reactions were incubated for 15 min at 37° C., then supplemented with 5 µl diluted DNA (100 ng total) and incubation at 37° C. continued for 90 min. The reactions were terminated by adding RNase A (Thermo Fisher Scientific) at a 1:100 dilution, then purifying the DNA using a PCR cleanup kit (LifeTechnologies) and eluting in 30 ul 10 mM Tris-Cl pH 8. Reactions were then stored at −20° C. until use.

Biotin Nick Translation

Nicked DNA was incubated with *E. coli* DNA polymerase I which has 5'>3' exonuclease activity, and is capable of initiating DNA synthesis at nicks, thus allowing it to replace nucleotides downstream of a nick with labeled nucleotides (in the case of this procedure, biotin-labeled nucleotides). Nick labeling reactions were performed in 20 ul of DNA polymerase buffer (NEB) with 1 unit of *E. coli* DNA polymerase I (NEB) and 0.02 mM each of dCTP, dGTP and dTTP, 0.01 mM of dATP and 0.01 mM biotin-C14 labeled dATP (LifeTechnologies) for 30 min at 25° C. Reactions were terminated by adding 1 mM EDTA.

Enrichment of Biotin Labeled DNA

Streptavidin C1 beads (5 ul per reaction, LifeTechnologies) were resuspended in 1 ml binding buffer (50 mM Tris-Cl pH 8, 1 mM EDTA, 0.1% Tween20), bound to a magnetic rack, and washed twice with binding buffer. Beads were then resuspended in 30 ul of binding buffer and mixed with the nick translation reaction, then incubated at 25° C. for 30 minutes. Beads were captured using the magnetic rack and washed four times with 0.5 ml binding buffer, then three times with 0.5 ml of 10 mM Tris-Cl pH 8. Beads were then resuspended in 20 ul 10 mM Tris-Cl pH 8, then used as templates for PCR to determine the proportion of test DNA and other DNA.

Example 3: Use of a Catalytically Dead Nucleic Acid-Guided Nuclease-Transposase Fusion to Insert Adaptors in Human Genomic Library Followed by Enriching for Specific SNPs (Protocol 3 for Capture of DNA)

In this example, catalytically dead nucleic acid-guided nuclease-transposase fusion protein (e.g. a dCas9-transposase fusion protein) is expressed and purified from *E. coli* as described for the Cas9 purification. The fusion protein is complexed with adapters (Nextera) then with guide NAs (e.g. gRNAs) targeting the regions of interest (e.g. human SNPs). Then the complex is added to human genomic DNA; regions of interest are targeted by the catalytically dead nucleic acid-guided nuclease, bringing the trasnposase-adapter complex in close proximity to the regions of interest, allowing insertion of the adapters. Human SNPs can then be amplified by PCR and then sequenced using MiSeq; thus human SNPs can be enriched from human genomic DNA.

Example 4: Using Catalytically Dead Nucleic Acid-Guided Nuclease and Nucleic Acid-Guided Nuclease to Protect Mitochondrial DNA and Digest Remaining Human Nuclear DNA from a Human Genomic DNA Library (Protocol 4 for Capture of DNA)

A human genomic DNA library with P5/P7 adapters from a clinical, forensic or environmental sample is obtained. To enrich for certain regions (e.g. SNPs) guide RNAs targeting these regions are made and incubated with catalytically dead nucleic acid-guided nuclease (e.g. dCas9) then added to the human genomic DNA library for 20 minutes at 37 C. Then, a library of guide NAs covering the human genome complexed with active nucleic acid-guided nuclease (e.g. Cas9) is added. The catalytically dead nucleic acid-guided nuclease will remain bound at the target locations and protect the regions of interests (e.g. SNPs) from being cleaved and becoming non PCR-amplifiable and sequence-able. Thus, the DNA of interest remains intact while all other DNA will be cleaved and eliminated. DNA of interest is recovered from the reactions using the PCR cleanup kit, PCR amplified and sequenced using MiSeq.

For proof of concept testing, mitochondrial DNA is enriched from a total human genomic DNA library. Mitochondrial specific guide RNAs are added to dCas9, then added to the library. Then, random guide RNAs complexed with Cas9 degrade any sequence, except for those inaccessible because already protected by bound dCas9. This allows enrichment of the mitochondrial DNA to levels far higher than the original 0.1-0.2%.

Example 5: Using a Nucleic Acid-Guided Nuclease Nickase (e.g. Cas9 Nickase) to Protect and then Enrich SNPs from Human Genomic DNA by Replacing Methylated DNA with Unmethylated DNA (Protocol 5 for Capture of DNA)

Overview

The objective of this method is to capture a region of interest from a library of human genomic DNA, as depicted in FIG. 11. As proof of principle, a test DNA containing a site for a nicking enzyme, NtBbvCI (NEB) was mixed at 1% or 5% into another pool of DNA that does not contain this site. The entire mixture was then treated with Dam methyltransferase to add methyl groups to all GATC sequences. Both test DNA and other DNA contain GATC motifs in their sequence. The mixture was then nicked using NtBbvCI, then incubated with DNA polymerase I and unlabeled nucleotides (dATP, dCTP, dGTP, dTTP), then heat inactivated at 75° C. for 20 minutes. The mixture is then digested with DpnI, which only digests methylated DNA; unmethylated or hemimethylated DNA will not be digested. FIG. 12 shows that methylation of test DNA renders it susceptible to DpnI mediated cleavage.

Expression and Purification of Cas9 Nickase

A mutant Cas9 nickase, a D10A mutant of *S. pyogenes* Cas9, can be produced and purified using the same procedures used to produce Cas9 as above.

Sequence Specific Cas9 Nickase-Mediated Nicking

Diluted guide RNA, targeting the following sequence 5'-GGATTTATACAGCACTTTAA-3' (SEQ ID NO: 29) (1 ul, equivalent to 2 pmol) is combined with 3 ul 10× Cas9 reaction buffer (NEB), 20 ul $H_2O$ and 1 ul of recombinant Cas9 Nickase enzyme (10 pmol/ul). This target sequence is only present on the target DNA (that makes either 5% or 1% of the total DNA). Reactions are incubated for 15 min at 37° C., then supplemented with 5 µl diluted DNA (100 ng total) and incubation at 37° C. continued for 90 min. The reactions are terminated by adding RNase A (Thermo Fisher Scientific) at a 1:100 dilution, then purifying the DNA using a PCR cleanup kit (LifeTechnologies) and eluting in 30 ul 10 mM Tris-Cl pH 8. Reactions are then stored at −20° C. until use.

Unlabeled DNA Nick Translation

Nicked DNA is incubated with *E. coli* DNA polymerase I which has 5'>3' exonuclease activity, and is capable of initiating DNA synthesis at nicks, thus allowing it to replace nucleotides downstream of a nick with labeled nucleotides (in the case of this procedure, biotin-labeled nucleotides). Nick labeling reactions are performed in 20 ul of DNA polymerase buffer (NEB) with 1 unit of *E. coli* DNA polymerase I (NEB) and 0.02 mM each of dATP, dCTP, dGTP and dTTP for 30 min at 25° C. Reactions are terminated by heat inactivation at 75° C. for 20 minutes.

Digestion with DpnI

Reactions are then incubated with DpnI (NEB) for one hour at 37° C. DNA is recovered using the PCR cleanup kit (LifeTechnologies) and then used as template for PCR using test DNA specific primers.

Example 6: Using a Nucleic Acid-Guided Nuclease Nickase (e.g. Cas9 Nickase) to Generate Long 3' Overhangs Flanking Regions of Interests, then Ligating Adapters to these Overhangs to Enrich Target DNA (Protocol 6 for Capture of DNA)

The objective of this method can be used to enrich a region of DNA, from any DNA source (e.g., library, genomic, or PCR), as depicted for example in FIG. 13. The nucleic acid-guided nuclease nickase (e.g. Cas9 Nickase)' can be targeted to proximal sites using two guide NAs (e.g. gRNAs) and, resulting in nicking of DNA at each location. Alternatively, an adapter can be ligated on only one side, then filled in, then an adapter can be ligated on the other side. The two nicks can be close to each other (e.g., within 10 to 15 bp). Single nicks may be generated in non-target molecules. Because of the proximity of the two nicking sites, a double stranded break can be created when the reaction is heated, e.g. to 65° C., resulting in long (e.g., 10-15 bp) 3' overhangs. These overhangs can be recognized by a thermostable single stranded DNA/RNA ligase, such as a Thermostable 5'App DNA/RNA ligase to allow for site-specific ligation of single stranded adapters. The ligase can, for example, only recognize long 3' overhangs, thus ensuring that adapters will not be ligated at other sites. This process can be repeated using the nucleic acid-guided nuclease nickase and guide NA targeting on the other side of the region of interest, followed by ligation as above using a second single stranded adapter. Once two adapters have been ligated on either side of the region of interest, the region can be amplified or sequenced directly.

What is claimed is:

1. A method comprising:
   (a) contacting a sample comprising a plurality of DNA sequences with a plurality of nucleic acid-guided nuclease nickase-gNA complexes, wherein the gNAs are gRNAs that are complementary to targeted sites of interest adjacent to regions of interest in a subset of the DNA sequences, thereby generating a plurality of nicked DNA molecules at sites adjacent to the regions of interest, and wherein the nucleic acid-guided nuclease nickase is a Cas9 nickase;
   (b) heating the sample to 65° C., thereby generating double-stranded breaks at the regions of interest with nicks adjacent thereto on both strands;
   (c) contacting the double-stranded breaks with a thermostable ligase and a plurality of adapters, thereby allowing ligation of adapters at these sites; and
   (d) repeating steps a-c to place a second adapter on the other side of the regions of interest.

2. The method of claim 1, wherein the DNA is from genomic DNA.

3. The method of claim 2, wherein the genomic DNA is human genomic DNA.

4. The method of claim 1, wherein the adapters from step (c) and the adapters from step (d) comprise single-stranded DNA molecules.

5. The method of claim 4, wherein the double-stranded breaks generated in step (b) comprise 3' single-stranded overhangs, and wherein the single-stranded DNA molecules are complementary to the 3' overhangs.

6. The method of claim 1, wherein the ligase is a thermostable single-stranded DNA/RNA ligase.

7. The method of claim 6, wherein the thermostable single-stranded DNA/RNA ligase is a 5' App thermostable DNA/RNA ligase.

8. The method of claim 1, wherein the Cas9 nickase is derived from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis* or *Corynebacter diphtheria*.

9. The method of claim 1, wherein the Cas9 nickase is derived from *Streptococcus pyogenes, Staphylococcus aureus* or *Streptococcus thermophiles*.

10. The method of claim 1, comprising (e) amplifying or sequencing the regions of interest.

* * * * *

UNITED STATES PATENT AND TRADEMARK OFFICE
CERTIFICATE OF CORRECTION

PATENT NO. : 10,538,758 B2  
APPLICATION NO. : 15/520052  
DATED : January 21, 2020  
INVENTOR(S) : Stephane B. Gourguechon et al.

Page 1 of 1

It is certified that error appears in the above-identified patent and that said Letters Patent is hereby corrected as shown below:

On the Title Page

Item (56) Column 1, Page 2, Line number 28:
"International Search Report dated Dec. 20, 2016, for PCT Application No. PCT/US2016/047631, filed on Aug. 18, 2016, 5 pagese."
Should read:
-- International Search Report dated Dec. 20, 2016, for PCT Application No. PCT/US2016/047631, filed on Aug. 18, 2016, 5 pages. --

Item (56) Column 2, Page 2, Line number 34-35:
"Dolinsek, J. et al (2013). "Depiction of unwanted nucleic acid templates by selective cleavage: LNAzyrnes, catalytically active oligonucleotides containing locked nucleic acids, open a new window for detecting rare microbial community members," *App. Environ. Microbiol.* 79:1534-1544."
Should read:
-- Dolinsek, J. et al (2013). "Depletion of unwanted nucleic acid templates by selective cleavage: LNAzymes, catalytically active oligonucleotides containing locked nucleic acids, open a new window for detecting rare microbial community members," *App. Environ. Microbiol.* 79:1534-1544. --

Item (56) Column 2, Page 2, Line number 51:
"Moylan, J.D. et al. (2012). "Selective depletion of rRNA enables whole transcriptome profiling of archival fixed tissue," *PioS One* 7:e42882. pp. 1-8 provided."
Should read:
-- Morlan, J.D. et al. (2012). "Selective depletion of rRNA enables whole transcriptome profiling of archival fixed tissue," *PloS One* 7:e42882. pp. 1-8 provided. --

Signed and Sealed this  
Thirty-first Day of March, 2020

Andrei Iancu  
*Director of the United States Patent and Trademark Office*

SEQUENCE LISTING

<160> NUMBER OF SEQ ID NOS: 29

<210> SEQ ID NO 1
<211> LENGTH: 29
<212> TYPE: DNA
<213> ORGANISM: Artificial Sequence
<220> FEATURE:
<223> OTHER INFORMATION: AUK sequencing read

<400> SEQUENCE: 1
cagtcctcca agttggtggt tgcccttaa                                  29

<210> SEQ ID NO 2
<211> LENGTH: 27
<212> TYPE: DNA
<213> ORGANISM: Artificial Sequence
<220> FEATURE:
<223> OTHER INFORMATION: Adapter sequence

<400> SEQUENCE: 2
gatcggaaga gcacacgtct gaactcc                                    27

<210> SEQ ID NO 3
<211> LENGTH: 56
<212> TYPE: DNA
<213> ORGANISM: Artificial Sequence
<220> FEATURE:
<223> OTHER INFORMATION: AUK sequencing read

<400> SEQUENCE: 3
cagtcctcca agttggtggt tgcccttaaa gtgctgtata aatcctacat caaatc    56

<210> SEQ ID NO 4
<211> LENGTH: 21
<212> TYPE: DNA
<213> ORGANISM: Artificial Sequence
<220> FEATURE:
<223> OTHER INFORMATION: Cas9/gRNA1 binding site

<400> SEQUENCE: 4
ttaaagtgct gtataaatcc t                                          21

<210> SEQ ID NO 5
<211> LENGTH: 47
<212> TYPE: DNA
<213> ORGANISM: Artificial Sequence
<220> FEATURE:
<223> OTHER INFORMATION: T7-gRNA oligonucleotide

<400> SEQUENCE: 5
gcctcgagct aatacgactc actataggga tttatacagc actttaa              47

<210> SEQ ID NO 6
<211> LENGTH: 47
<212> TYPE: DNA
<213> ORGANISM: Artificial Sequence
<220> FEATURE:
<223> OTHER INFORMATION: T7-gRNA oligonucleotide

<400> SEQUENCE: 6
gcctcgagct aatacgactc actatagggt cttttggtc ctcgaag               47

<210> SEQ ID NO 7
<211> LENGTH: 94
<212> TYPE: DNA
<213> ORGANISM: Artificial Sequence
<220> FEATURE:
<223> OTHER INFORMATION: stglR oligonucleotide

<400> SEQUENCE: 7
gttttagagc tagaaatagc aagttaaaat aaggctagtc cgttatcaac ttgaaaaagt    60
ggcaccgagt cggtgctttt tttggatccg atgc    94

<210> SEQ ID NO 8
<211> LENGTH: 22
<212> TYPE: DNA
<213> ORGANISM: Artificial Sequence
<220> FEATURE:
<223> OTHER INFORMATION: ForT7 primer

<400> SEQUENCE: 8
gcctcgagct aatacgactc ac    22

<210> SEQ ID NO 9
<211> LENGTH: 21
<212> TYPE: DNA
<213> ORGANISM: Artificial Sequence
<220> FEATURE:
<223> OTHER INFORMATION: gRU primer

<400> SEQUENCE: 9
aaaaaaagca ccgactcggt g    21

<210> SEQ ID NO 10
<211> LENGTH: 47
<212> TYPE: DNA
<213> ORGANISM: Artificial Sequence
<220> FEATURE:
<223> OTHER INFORMATION: T7-1-F primer

<400> SEQUENCE: 10
gcctcgagct aatacgactc actataggct tggattagcg tttagaa    47

<210> SEQ ID NO 11
<211> LENGTH: 48
<212> TYPE: DNA
<213> ORGANISM: Artificial Sequence
<220> FEATURE:
<223> OTHER INFORMATION: T7-13-F primer

<400> SEQUENCE: 11
gcctcgagct aatacgactc actataggct cttaaaacta ggcggcta    48

<210> SEQ ID NO 12
<211> LENGTH: 47
<212> TYPE: DNA
<213> ORGANISM: Artificial Sequence
<220> FEATURE:
<223> OTHER INFORMATION: T7-39-F primer

<400> SEQUENCE: 12
gcctcgagct aatacgactc actatagatt tacactcaca acaccct    47

<210> SEQ ID NO 13
<211> LENGTH: 47
<212> TYPE: DNA
<213> ORGANISM: Artificial Sequence
<220> FEATURE:
<223> OTHER INFORMATION: T7-41-F primer

<400> SEQUENCE: 13
gcctcgagct aatacgactc actatagaac agctatccat tggtctt    47

<210> SEQ ID NO 14
<211> LENGTH: 47
<212> TYPE: DNA
<213> ORGANISM: Artificial Sequence
<220> FEATURE:
<223> OTHER INFORMATION: T7-43-F primer

<400> SEQUENCE: 14
gcctcgagct aatacgactc actataggca gccggaagcc tattcgc    47

<210> SEQ ID NO 15
<211> LENGTH: 47
<212> TYPE: DNA
<213> ORGANISM: Artificial Sequence
<220> FEATURE:
<223> OTHER INFORMATION: T7-61-F primer

<400> SEQUENCE: 15
gcctcgagct aatacgactc actataggta atgaggatgt aagcccg    47

<210> SEQ ID NO 16
<211> LENGTH: 47
<212> TYPE: DNA
<213> ORGANISM: Artificial Sequence
<220> FEATURE:
<223> OTHER INFORMATION: T7-63-F primer

<400> SEQUENCE: 16
gcctcgagct aatacgactc actatagata tttacaagag gaaaacc    47

<210> SEQ ID NO 17
<211> LENGTH: 48
<212> TYPE: DNA
<213> ORGANISM: Artificial Sequence
<220> FEATURE:
<223> OTHER INFORMATION: T7-65-F primer

<400> SEQUENCE: 17
gcctcgagct aatacgactc actataggtt tgaagcttag ggagagct    48

<210> SEQ ID NO 18
<211> LENGTH: 47
<212> TYPE: DNA
<213> ORGANISM: Artificial Sequence
<220> FEATURE:
<223> OTHER INFORMATION: T7-67-F primer

<400> SEQUENCE: 18
gcctcgagct aatacgactc actataggta tggctttgaa gaaggcg    47

<210> SEQ ID NO 19
<211> LENGTH: 47
<212> TYPE: DNA
<213> ORGANISM: Artificial Sequence
<220> FEATURE:
<223> OTHER INFORMATION: T7mtgRNA3 primer

<400> SEQUENCE: 19
gcctcgagct aatacgactc actatagtag atgacgggtt gggccag    47

<210> SEQ ID NO 20
<211> LENGTH: 47
<212> TYPE: DNA
<213> ORGANISM: Artificial Sequence

```
<220> FEATURE:
<223> OTHER INFORMATION: T7mtgRNA7 primer

<400> SEQUENCE: 20
gcctcgagct aatacgactc actatagagc tttacagtgg gctctag        47

<210> SEQ ID NO 21
<211> LENGTH: 47
<212> TYPE: DNA
<213> ORGANISM: Artificial Sequence
<220> FEATURE:
<223> OTHER INFORMATION: T7mtgRNA11 primer

<400> SEQUENCE: 21
gcctcgagct aatacgactc actatagatg gcagcttctg tggaacg        47

<210> SEQ ID NO 22
<211> LENGTH: 47
<212> TYPE: DNA
<213> ORGANISM: Artificial Sequence
<220> FEATURE:
<223> OTHER INFORMATION: T7mtgRNA15 primer

<400> SEQUENCE: 22
gcctcgagct aatacgactc actataggtg gtaagggcga tgagtgt        47

<210> SEQ ID NO 23
<211> LENGTH: 47
<212> TYPE: DNA
<213> ORGANISM: Artificial Sequence
<220> FEATURE:
<223> OTHER INFORMATION: T7mtgRNA31 primer

<400> SEQUENCE: 23
gcctcgagct aatacgactc actatagtcc ataacgctcc tcatact        47

<210> SEQ ID NO 24
<211> LENGTH: 47
<212> TYPE: DNA
<213> ORGANISM: Artificial Sequence
<220> FEATURE:
<223> OTHER INFORMATION: T7mtgRNA33 primer

<400> SEQUENCE: 24
gcctcgagct aatacgactc actatagtct cccttcacca tttccga        47

<210> SEQ ID NO 25
<211> LENGTH: 20
<212> TYPE: DNA
<213> ORGANISM: Artificial Sequence
<220> FEATURE:
<223> OTHER INFORMATION: control guide RNA target sequence

<400> SEQUENCE: 25
ggatttatac agcactttaa        20

<210> SEQ ID NO 26
<211> LENGTH: 16
<212> TYPE: DNA
<213> ORGANISM: Artificial Sequence
<220> FEATURE:
<223> OTHER INFORMATION: TestDNA-F primer

<400> SEQUENCE: 26
atgccgcagc acttgg        16
```

```
<210> SEQ ID NO 27
<211> LENGTH: 20
<212> TYPE: DNA
<213> ORGANISM: Artificial Sequence
<220> FEATURE:
<223> OTHER INFORMATION: P5 primer

<400> SEQUENCE: 27
aatgatacgg cgaccaccga                                              20

<210> SEQ ID NO 28
<211> LENGTH: 21
<212> TYPE: DNA
<213> ORGANISM: Artificial Sequence
<220> FEATURE:
<223> OTHER INFORMATION: P7 primer

<400> SEQUENCE: 28
caagcagaag acggcatacg a                                            21

<210> SEQ ID NO 29
<211> LENGTH: 20
<212> TYPE: DNA
<213> ORGANISM: Artificial Sequence
<220> FEATURE:
<223> OTHER INFORMATION: gRNA targeting sequence

<400> SEQUENCE: 29
ggatttatac agcactttaa                                              20
```